US008854730B2

(12) United States Patent
Wang et al.

(10) Patent No.: US 8,854,730 B2
(45) Date of Patent: Oct. 7, 2014

(54) NEGATIVELY BIREFRINGENT POLYESTERS AND OPTICAL FILMS

(75) Inventors: Lei Wang, San Jose, CA (US); David T. Yust, Woodbury, MN (US); George W. Griesgraber, Eagan, MN (US); Stephen A. Johnson, Woodbury, MN (US); David S. Hays, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 137 days.

(21) Appl. No.: 13/303,881

(22) Filed: Nov. 23, 2011

(65) Prior Publication Data
US 2012/0170118 A1  Jul. 5, 2012

Related U.S. Application Data

(60) Provisional application No. 61/428,481, filed on Dec. 30, 2010.

(51) Int. Cl.
| | | |
|---|---|---|
| *G02B 5/30* | (2006.01) | |
| *C08G 63/185* | (2006.01) | |
| *G02B 5/32* | (2006.01) | |
| *C07C 33/36* | (2006.01) | |
| *C07C 57/50* | (2006.01) | |
| *C07C 69/616* | (2006.01) | |
| *C08G 63/193* | (2006.01) | |
| *C08J 7/04* | (2006.01) | |
| *G02B 1/04* | (2006.01) | |

(52) U.S. Cl.
CPC ............... *C08G 63/185* (2013.01); *G02B 5/32* (2013.01); *C07C 33/36* (2013.01); *C07C 57/50* (2013.01); *C07C 69/616* (2013.01); *C07C 2103/26* (2013.01); *C08G 63/193* (2013.01); *C08J 7/047* (2013.01); *C08J 2367/02* (2013.01); *C08J 2467/02* (2013.01); *G02B 1/04* (2013.01); *G02B 5/3083* (2013.01)
USPC .................................................. 359/489.01

(58) Field of Classification Search
CPC ...... C08J 5/18; C08J 2301/10; C08J 2367/03; C08J 2301/12; C08J 2301/14; C08J 2367/00; C08J 2367/02; C08J 2369/00; C08J 7/047; C08J 7/123
See application file for complete search history.

(56) References Cited

U.S. PATENT DOCUMENTS

| | | |
|---|---|---|
| 2,339,373 A | 1/1944 | Bruson |
| 2,732,398 A | 1/1956 | Brice |

(Continued)

FOREIGN PATENT DOCUMENTS

| | | |
|---|---|---|
| DE | 1941227 | 2/1970 |
| GB | 1243145 | 8/1971 |

(Continued)

OTHER PUBLICATIONS

Alder et al, "Conformational control by quaternary centres: theory, database evidence and application to polymers" J. Chem. Soc., Perkin Trans. 2, 1998, pp. 2083-2107.

(Continued)

*Primary Examiner* — Derek S Chapel
(74) *Attorney, Agent, or Firm* — Carolyn A. Fischer

(57) ABSTRACT

Presently described are multilayer optical films, oriented polyester films, negatively birefringent copolyester polymers, fluorene monomers, and polyester polymers prepared from such fluorene monomers. In one embodiment, the multilayer optical film comprises at least one first birefringent optical layer; and at least one second optical layer having a lower birefringence than the first optical layer; wherein at least one of the optical layers comprises a negatively birefringent polyester polymer comprising a backbone and repeat units comprising at least one pendent aromatic group that is conformationally locked relative to the backbone.

26 Claims, 1 Drawing Sheet

(56) References Cited

U.S. PATENT DOCUMENTS

| | | | |
|---|---|---|---|
| 3,114,768 | A | 12/1963 | Fritz |
| 3,184,434 | A | 5/1965 | Horn |
| 3,274,240 | A | 9/1966 | Fritz |
| 3,280,169 | A | 10/1966 | Horn |
| 3,426,069 | A | 2/1969 | Fritz |
| 3,641,115 | A | 2/1972 | Peck |
| 4,904,755 | A | 2/1990 | Machell |
| 5,677,050 | A | 10/1997 | Bilkadi |
| 5,882,774 | A | 3/1999 | Jonza |
| 5,999,317 | A | 12/1999 | Whitney |
| 6,012,820 | A | 1/2000 | Weber |
| 6,024,455 | A | 2/2000 | O'Neill |
| 6,045,894 | A | 4/2000 | Jonza |
| 6,049,419 | A | 4/2000 | Wheatley |
| 6,053,795 | A | 4/2000 | Whitney |
| 6,082,876 | A | 7/2000 | Hanson |
| 6,096,375 | A | 8/2000 | Ouderkirk |
| 6,120,026 | A | 9/2000 | Whitney |
| 6,157,486 | A | 12/2000 | Benson, Jr. |
| 6,368,699 | B1 | 4/2002 | Gilbert |
| 6,451,414 | B1 | 9/2002 | Wheatley |
| 6,455,140 | B1 | 9/2002 | Whitney |
| 6,459,514 | B2 | 10/2002 | Gilbert |
| 6,475,609 | B1 | 11/2002 | Whitney |
| 6,531,230 | B1 | 3/2003 | Weber |
| 6,609,795 | B2 | 8/2003 | Weber |
| 6,641,280 | B2 | 11/2003 | Hanson |
| 6,749,427 | B1 | 6/2004 | Bretscher |
| 6,783,349 | B2 | 8/2004 | Neavin |
| 6,788,463 | B2 | 9/2004 | Merrill |
| 6,797,366 | B2 | 9/2004 | Hanson |
| 6,808,658 | B2 | 10/2004 | Stover |
| 6,827,886 | B2 | 12/2004 | Nevin |
| 6,830,713 | B2 | 12/2004 | Hebrink |
| 6,926,410 | B2 | 8/2005 | Weber |
| 7,077,649 | B2 | 7/2006 | Bretscher |
| 7,385,763 | B2 | 6/2008 | Nevitt |
| 7,418,202 | B2 | 8/2008 | Biernath |
| 7,843,637 | B2 | 11/2010 | Biernath |
| 7,851,054 | B2 | 12/2010 | Weber |
| 2005/0286001 | A1 | 12/2005 | Elman |
| 2007/0087132 | A1 | 4/2007 | Greener |

FOREIGN PATENT DOCUMENTS

| | | |
|---|---|---|
| WO | WO 99/36248 | 7/1999 |
| WO | WO 2007/075264 | 7/2007 |

OTHER PUBLICATIONS

Boese et al., "Chain Orientation and Anisotropies in Optical and Dielectric Properties in Thin Films of Stiff Polyimides", J. Polym. Sci.; Part B, vol. 30: 1321-1327 (1992).

Zang et al., "Giant anisotropies in the dielectric properties of quasiepitaxial crystalline organic semiconductor thin films"; Applied Physics Letters, 59, 823-825 (1991).

Bruson, "Cyanoethylation of Active Methylene Groups, The Chemistry of Acrylonitrile", J. Am. Chem. Soc., 64, (1942), 2457-2461.

Baldwin, "The Synthesis of Spiro[cyclohexane-1-9'-fluorene] and Related Compounds", J. Org. Chem., 26, (1961), 3280-3287.

Niederprum et al., "Hydroxyalkylierung von Perfluoralkansulfonamiden", Liebigs Ann. Chem. 1973, 11-19.

Nakano et al., "Poly(2,7-di-*n*-pentyldibenzofulvene) showing chiroptical properties in the solid state based purely on a chiral conformation", Chem. Commun., 2004, 144-145.

Fritz et al., "The Base-Catalyzed Alkylation of Fluorene and Indene with Alcohols and Diols", J. Org. Chem., 30, (1965) 2540-2542.

Rathore et al., "Synthesis, Structure, and Evaluation of the Effect of Multiple Stacking on the Electron-Donor Properties of -Stacked -Polyfluorenes", J. Am. Chem. Soc. vol. 125, No. 29, (2003), 8712-8713.

Bergman et al., "Synthesis of Fluoranthene and its Derivatives", J. Am. Chem. Soc., 71 (6), 1949; 1917-1918.

Bavin, "Aliphatic Chemistry of Fluorene, Part IX. Some Bifunctional Derivatives" Canadian Journal of Chemistry, 42 (1964) 1409-1417.

Rubin et al., "Alkylation of Fluorene with Alchols and Their Alkoxides. III. Polyhydroxy Compounds" Journal of American Chemical Society, vol. 22 (1957) 1623-1625.

Wawzonek et al., "The Acid-catalyzed Reaction of 9-Fluorenol with 9-Alkylidenefluorenes", Journal of the American Chemical Society, vol. 78 (1956) 3530-3533.

Alder et al., "Polymers and Oligomers with Transverse Aromatic Groups and Tightly Controlled Chain Conformations" Chemical Communications (1998) 309-310.

Campbell et al., "Synthesis of Fluorantheses, Part II. Michael Addition of Vinyl Cyanide to Fluorene-9-carboxylic Esters" Journal of the Chemical Society, (1949) 2623-2626.

Fritz et al., "The Michael Reaction of Acrylate Salts", Journal of Organic Chemistry, vol. 33, No. 6 (Jun. 1968) 2577-2580.

Schlenk et al., "Über Reindarstellung und Reaktionen einiger krystallisierter Enolate", Apr. 1931, 135-154.

Bavin, "Characterization of Alkyl Halides", Analytical Chemistry, 32, (1960) 554-556.

Hashimoto et al., Michael Reaction of Fluorenes with a,β-Unsaturated Esters and Ketones Catalyzed by Tetra-*n*-butylammonium Fluoride, Synthesis: English 2; 1984 164-166.

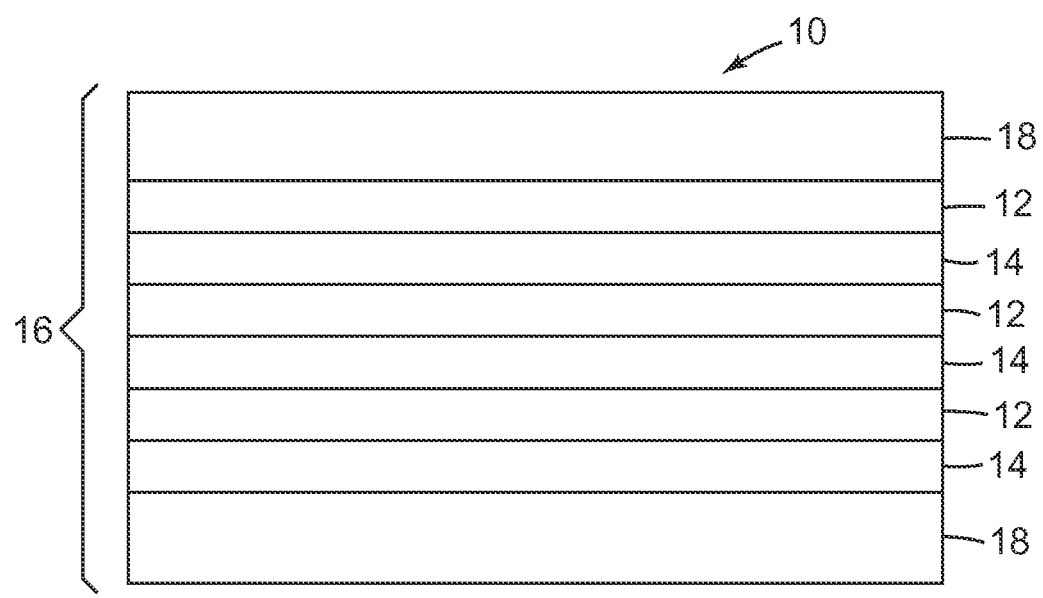

NEGATIVELY BIREFRINGENT POLYESTERS AND OPTICAL FILMS

RELATED APPLICATION DATA

This application claims the benefit of U.S. Provisional Application Ser. No. 61/428,481, filed Dec. 30, 2010.

BACKGROUND

Polymeric films are used in a wide variety of applications. Multilayer polymeric optical films are widely used for various purposes, including as mirrors and polarizers. These films often have extremely high reflectivity, while being lightweight and resistant to breakage. Examples of a wide variety of multilayer films are included in the commonly assigned U.S. Pat. No. 5,882,774, entitled "Optical Film". Exemplary applications include compact electronic displays, including liquid crystal displays (LCDs) placed in mobile telephones, personal data assistants, computers, televisions and other devices.

One type of polymer that is useful in creating polarizers or mirror films is a polyester. One example of a polyester-based polarizer includes a stack of polyester layers of differing composition. Such stacks are also commonly referred to as a multilayer reflective film. The multilayer reflective films may also include one or more additional layers which, for example, cover at least one surface of the stack of layers to prevent damage to the stack during or after processing.

A polyester is prepared by reactions of one or more different carboxylate monomers (e.g., compounds with two or more carboxylic acid or ester functional groups) with one or more different glycol monomers (e.g., compounds with two or more hydroxyl functional groups). The properties of a polyester polymer or film vary with the particular choice of kind and amount of monomer molecules.

U.S. Pat. No. 4,904,755 describes low birefringent polyesters that are useful in optical devices. The polyesters include units having opposite optical anisotropies. By varying the ratio of the units in the copolymer, the birefringence of an article made from the copolymer can be controlled as desired. The polyester is a substantially optically anisotropic polyester having diol repeating units derived from 9,9-bis(4-hydroxyphenyl)fluorene and at least about 40% by weight of the diacid repeating units derived from aliphatic or cycloaliphatic dicarboxylic acids, the remainder of the diacid repeating units being derived from aromatic dicarboxylic acids.

Diol repeat units derived from 9,9-bis(4-hydroxyphenyl) fluorene is one example of a class of structures commonly known as Cardo structures.

SUMMARY

Presently described are multilayer optical films, oriented polyester films, negatively birefringent copolyester polymers, fluorene monomers, and polyester polymers prepared from such fluorene monomers.

BRIEF DESCRIPTION OF THE DRAWINGS

FIG. 1 is a cross-sectional view of one embodiment of a multilayer optical film.

DETAILED DESCRIPTION

As used in this application:

"index of refraction" refers to a refractive index of a material in the plane of the material with respect to light at 633 nm and normal incidence, unless otherwise indicated;

"birefringent" means that the indices of refraction in orthogonal x, y, and z directions are not all the same. For the polymer layers described herein, the axes are selected so that x and y axes are in the plane of the layer and the z axis is normal to the plane of the layer and typically corresponds to the thickness or height of the layer. For a positively birefringent material, where a refractive index in one in-plane direction is larger than a refractive index in another in-plane direction, the x-axis is generally chosen to be the in-plane direction with the largest index of refraction, which sometimes corresponds to one of the directions in which the optical film is oriented (e.g., stretched). Birefringence may either be positive or negative. Birefringence values are reported with respect to light at 633 nm and normal incidence, unless otherwise indicated;

"positive birefringence" is defined as when the direction of the electric field axis for linearly polarized light experiences the highest refractive index when it is parallel to the polymer's orientation or aligning surface. For a positively birefringent first material, the direction of highest in-plane refractive index, the first in-plane direction, coincides with the draw direction, while the direction of lowest in-plane refractive index for the first material, the second in-plane direction, is perpendicular to this direction. Examples of positively birefringent polymers include PEN and PET;

"negative birefringence" is defined as when the direction of the electric field axis for linearly polarized light experiences the lowest refractive index when it is parallel to the polymer's orientation or aligning surface. An example of a negatively birefringent polymer is syndiotactic polystyrene;

"high refractive index" and "low refractive index" are relative terms; when two layers are compared in at least one direction of interest, the layer that has a greater in-plane refractive index is the high refractive index layer, and the layer that has a lower in-plane refractive index is the low refractive index layer;

"polymer" means, unless otherwise indicated, polymers and copolymers (i.e., polymers formed from two or more monomers or comonomers, including terpolymers, for example), as well as copolymers or polymers that can be formed in a miscible blend by, for example, coextrusion or reaction, including transesterification, for example. Block, random, graft, and alternating polymers are included, unless indicated otherwise;

"polyester polymer" means, any polymer wherein the repeat units are joined by ester linkages. In some embodiments, the polyester polymer is a homopolymer (i.e. homopolyester) derived from a single carboxylate monomer and a single glycol monomer. In other embodiments, the polyester polymer is a copolymer (i.e. copolyester) derived from at least two different carboxylate monomers and a single glycol monomer, at least two different glycol monomers and a single carboxylate monomer, or a combination of two or more different carboxylate monomers and two or more different glycol monomers;

"constrained uniaxial stretching" refers to a film stretching process in which external stress is applied to introduce dimensional change in primarily two directions, in-plane stretching direction (i.e. x) and normal to in-plane (i.e. z). Specifically, it refers to a dimensional elongation in the in-plane stretching direction while substantially maintaining the film width in the in-plane non-stretching direction. As a result, the film thickness reduction usually scales with the film draw ratio and the structure is largely planar; and "unconstrained uniaxial stretching" refers to a film stretching process in which external stress is applied to introduce dimensional change in all three directions. The width of the film is usually small compare to the length of the stretching direction. Specifically, it refers to a dimensional elongation in the in-plane stretching direction while allowing both the film thickness and the film width to reduce. As a result, the film thickness reduction is less than constrained uniaxial stretched film at the same draw ratio. Furthermore, the structure of the film is more cylindrical and fiber like.

In some embodiments, multilayer films are described. Multilayer film embodiments include a film having two or more layers. Multilayer optical films are useful, for example, as highly efficient mirrors and/or polarizers. Multilayer optical films generally exhibit relatively low absorption of incident light, as well as high reflectivity for off-axis as well as normal light rays.

The multilayer optical films described herein generally comprise at least one first birefringent optical layer and at least one second optical layer having a lower birefringence than the first optical layer.

FIG. 1 shows a multilayer polymer film 10 which may be used, for example, as an optical polarizer or mirror. The film 10 includes one or more first optical layers 12, one or more second optical layers 14, and optionally one or more (e.g. non-optical) additional layers 18. FIG. 1 includes a multilayer stack having alternating layers 12, 14 of at least two materials. In one embodiment, the materials of layers 12 and 14 are polymeric. In general, U.S. Pat. No. 6,827,886, entitled "Method for making multilayer optical films," hereby incorporated by reference, describes methods that can be adapted for making multilayer film 10. In addition, although film 10 and layers 12, 14 are illustrated as having planar surfaces, at least one surface of the film 10 or layers 12, 14 or an additional layer may be structured.

An in-plane index of refraction n1 of high refractive index layer 12 is higher than an in-plane index of refraction n2 of low refractive index layer 14. The difference in refractive index at each boundary between layers 12, 14 causes part of light ray to be reflected. The transmission and reflection characteristics of multilayer film 10 is based on coherent interference of light caused by the refractive index difference between layers 12, 14 and the thicknesses of layers 12, 14. When the effective indices of refraction (or in-plane indices of refraction for normal incidence) differ between layers 12, 14, the interface between adjacent layers 12, 14 forms a reflecting surface. The reflective power of interface surface depends on the square of the difference between the effective indices of refraction of the layers 12, 14 (e.g., $(n1-n2)^2$). By increasing the difference in the indices of refraction between the layers 12, 14, improved optical power (higher reflectivity), thinner films (thinner or fewer layers), and broader bandwidth performance can be achieved. Multilayer film 10 can thus be made useful as a reflective polarizer or mirror, for example. The refractive index difference in an exemplary embodiment is at least about 0.05, preferably greater than about 0.10, more preferably greater than about 0.20 and even more preferably greater than about 0.30.

In one embodiment, the materials of layers 12, 14 inherently have differing indices of refraction. In another embodiment, at least one of the materials of layers 12, 14 has the property of stress induced birefringence, such that the index of refraction (n) of the material is affected by the stretching process. By stretching multilayer film 10 over a range of uniaxial to biaxial orientations, films can be created with a range of reflectivities for differently oriented plane-polarized incident light.

In exemplary embodiments, multilayer film 10 includes tens, hundreds or thousands of layers, and each layer can be made from any of a number of different materials. The characteristics which determine the choice of materials for a particular stack depend upon the desired optical performance of multilayer film 10. Multilayer film 10 can contain as many materials as there are layers in the stack. However, for ease of illustration, exemplary embodiments of optical thin film stacks show only a few different materials.

In one embodiment, the number of layers in multilayer film 10 is selected to achieve the desired optical properties using the minimum number of layers for reasons of film thickness, flexibility and economy. In the case of reflective films such as polarizers and mirrors, the number of layers is preferably less than about 2,000, more preferably less than about 1,000, and even more preferably less than about 500.

In some embodiments, the multilayer polymer film further comprises optional additional non-optical or optical layers. The additional layers 18 are polymer layers that are disposed within the stack 16. Such additional layers may protect the optical layers 12, 14 from damage, aid in the co-extrusion processing, and/or to enhance post-processing mechanical properties. The additional layers 18 are often thicker than the optical layers 12, 14. The thickness of the additional (e.g. skin) layers 18 is usually at least two times, preferably at least four times, and more preferably at least ten times, the thickness of the individual optical layers 12, 14. The thickness of the additional layers 18 may be varied to make a multilayer polymer film 10 having a particular thickness. Typically, one or more of the additional layers 18 are placed so that at least a portion of the light to be transmitted, polarized, and/or reflected by the optical layers 12, 14, also travels through the additional layers (i.e., the additional layers are placed in the path of light which travels through or is reflected by the optical layers 12, 14).

One embodiment of multilayer film 10 comprises multiple low/high index pairs of film layers, wherein each low/high index pair of layers has a combined optical thickness of ½ the center wavelength of the band it is designed to reflect. Stacks of such films are commonly referred to as quarterwave stacks. For multilayer optical films concerned with the visible and the near infrared wavelengths, a quarterwave stack design results in each of the layers 12, 14 in the multilayer stack having an average thickness of not more than about 0.5 micrometers. In other exemplary embodiments, different low-high index pairs of layers may have different combined optical thicknesses, such as where a broadband reflective optical film is desired.

In those applications where reflective films (e.g. mirrors or polarizers) are desired, the desired average transmission for light of each polarization and plane of incidence generally depends upon the intended use of the reflective film. One way to produce a multilayer mirror film is to biaxially stretch a multilayer stack. For a high efficiency reflective film, average transmission along each stretch direction at normal incidence over the visible spectrum (about 380-750 nm) is desirably less than about 10 percent (reflectance greater than about 90 percent), preferably less than about 5 percent (reflectance greater than about 95 percent), more preferably less than about 2 percent (reflectance greater than about 98 percent), and even more preferably less than about 1 percent (reflectance greater than about 99 percent). The average transmission at about 60 degrees from the normal over the visible spectrum is desirably less than about 20 percent (reflectance greater than about 80 percent), preferably less than about 10 percent (reflectance greater than about 90 percent), more preferably less than about 5 percent (reflectance greater than about 95 percent), and even more preferably less than about 2 percent (reflectance greater than about 98 percent), and even more preferably less than about 1 percent (reflectance greater than about 99 percent). Some examples of mirror films are further described in U.S. Pat. No. 5,882,774 (Jonza et al.).

In addition, asymmetric reflective films (such as films resulting from unbalanced biaxial stretching) may be desirable for certain applications. In that case, average transmission along one stretch direction may be desirably less than, for example, about 50 percent, while the average transmission along the other stretch direction may be desirably less than, for example, about 20 percent, over a bandwidth of, for example, the visible spectrum (about 380-750 nm), or over the visible spectrum and into the near infrared (e.g., about 380-850 nm).

Multilayer optical films can also be designed to operate as reflective polarizers. One way to produce a multilayer reflective polarizer is to uniaxially stretch a multilayer stack. The resulting reflective polarizers have high reflectivity for light with its plane of polarization parallel to a first in-plane axis (usually, in the stretch direction) for a broad range of angles of incidence, and simultaneously have low reflectivity and high transmissivity for light with its plane of polarization parallel to a second in-plane axis that is orthogonal to the first in-plane axis (usually, in the non-stretch direction) for a broad range of angles of incidence. By controlling the three indices of refraction of each film, nx, ny and nz, the desired polarizer behavior can be obtained. See, for example U.S. Pat. No. 5,882,774 (Jonza et al.).

The optical layers 12, 14 and the optional additional layers 18 of the multilayer polymer film 10 are typically composed of polymers such as polyesters.

Polyesters include carboxylate and glycol subunits and are generated by reactions of carboxylate monomer molecules with glycol monomer molecules. Each carboxylate monomer molecule has two or more carboxylic acid or ester functional groups and each glycol monomer molecule has two or more hydroxy functional groups. The carboxylate monomer molecules may all be the same or there may be two or more different types of molecules. The same applies to the glycol monomer molecules. For embodiments wherein the copolyester contains more than one type of glycol or carboxylate comonomer, the copolyester may be a block or random copolyester. The properties of a polymer layer or film vary with the particular choice of monomer molecules of the polyester.

In favored embodiments, multilayer optical films are described wherein at least one of the optical layers comprises a negatively birefringent polyester polymer. Without intending to be bound by theory, it is surmised that the negative birefringence is provided at least in part, by the polyester polymer comprising repeat units having at least one pendent aromatic group, such as fluorene. Although a pendent fluorene group can provide slight negative birefringence (e.g. −0.0005 as illustrated by Example 17), in favored embodiments, the pendent aromatic (e.g. fluoroene) group is conformationally locked relative to the polyester polymer backbone. By "conformationally locked", it is meant that the pendant aromatic group is unable to substantially rotate relative to the polyester polymer backbone. Thus, parallel sides of the conformationally locked aromatic group (e.g. aromatic ring(s)) are orthogonal to the polyester backbone. It has been found that when the pendent aromatic (e.g. fluorene) group is conformationally locked, the birefringence can be increasingly negative. For example, the negative birefringence may be at least −0.0010 (e.g. twice the magnitude of Example 17), or at least −0.0050, or at least −0.0100.

In some embodiments, the pendant aromatic group may be conformationally locked, at least in part, due to steric hindrance. For example, the aromatic group may comprise "bulky" substituents that prevent rotation of the aromatic group.

In favored embodiments, the pendant aromatic group is conformationally locked due to covalent bonding. Conformationally locked aromatic groups typically comprise sufficient bonds between the carbon atoms of the aromatic ring(s) and the backbone of the polyester polymer to prevent rotation. Conformationally locked (e.g. aromatic) groups are known in the art, such as described in *Conformation Control by Quaternary Centres: Theory, Database Evidence, and Application to Polymers*, J. Chem. Soc., Perkin Trans. 2, 1998, pp. 2083-2107. One favored conformationally locked aromatic group is fluorene (i.e. alpha-diphenylene methane) wherein there are two single bonds between the methane group of the fluorene molecule and the backbone of the polyester polymer.

Provided that the pendent aromatic group (e.g. fluorene group) is bonded directly to the backbone or bonded by a linking group having a single orientation in space, parallel sides of the conformationally locked aromatic group (e.g. conformationally locked aromatic rings of fluorene) are orthogonal to the polyester polymer backbone.

Cardo groups comprise phenyl linking groups. Such phenyl groups are not conformationally locked. Rather one of the phenyl rings is slightly twisted or canted in relation to the other phenyl ring as a consequence of steric crowding. The resulting conformation has a dihedral angle of less than 90 degrees. Due to the twisting of the phenyl linking groups of Cardo groups, parallel sides of the pendent aromatic (e.g. fluorene) group are not orthogonal to the polyester backbone.

Since aromatic groups often can have more than one orientation in space, the linking group between the pendent conformationally locked (e.g. fluorene) group is typically a non-aromatic linking group such as a straight-chain alkylene optionally comprising heteroatoms. In some embodiments, an ethylene linkage is present between the pendent fluoroene group and the ester group of the polyester backbone.

In the multilayer optical films described herein, typically the second (i.e. lower birefringence) layer comprises a sufficient concentration of repeat units comprising such pendent fluorene or other conformationally locked aromatic group to provide the desired negative birefringence.

The polyester polymeric materials are described herein with reference to the overall composition i.e. 100 mol % units derived from 50 mol % carboxylate units and 50 mol % glycol units. Polyester polymeric materials are also described herein with reference to the mol % of carboxylate subunits and mol % glycol subunits (i.e. 100 mol % of carboxylate subunits are reacted with 100 mol % of glycol subunits in the preparation of the copolyester).

The polyester polymer is derived from at least one diacid, diester, diol, or mixture thereof comprising at least one pendent fluorene group or other conformationally locked aromatic group. Relatively high negative birefringence can be obtained when at least 40 mol %, or 45 mol %, or 50 mol % to 100 mol % of the units (i.e. the combination of carboxylate units and glycol units) comprise at least one pendent conformationally locked (e.g. fluorene) aromatic group. However, sufficiently low birefringence can be obtained with a lower molar percentage of repeat units comprising at least one pendent fluorene or other conformationally locked aromatic group. For example, the polyester polymer or second (e.g. low birefringence) layer may comprise at least 20 mol %, or 25 mol %, or 30 mol %, or 35 mol % of carboxylate units and/or glycol units that comprise at least one pendent fluorene or other conformationally locked aromatic group.

The negatively birefringent polyester materials may also be utilized at even lower concentrations in the first (i.e. higher birefringence) layer or second (i.e. lower birefringence) layer of the multilayer film. For example, the first (i.e. higher birefringence) layer may contain a few molar percentage (e.g. 2 or 3 mol %) up to 5 mol %, 10 mol %, or 15 mol % of repeat units comprising at least one pendent fluorene or other conformationally locked aromatic group blended with another polymer (such as a PEN copolyester) for the purpose of improving adhesion to the second (i.e. lower birefringence) layer having a relatively high molar percentage of such repeat units. Further, either the first or second layer may contain a few molar percentage (e.g. 2 or 3 mol %) up to 5 mol %, 10 mol %, 15 mol %, or 20 mol % of repeat units comprising at least one pendent fluorene or other conformationally locked aromatic group blended with another polymer (such as another polyester) for the purpose of adjusting or "tuning" the birefringence of a particular layer.

The polyester polymer described herein comprises repeat units that comprise a monofluorene, a difluorene, or a combination thereof. Hence, the polyester polymer is derived from at least one diacid, diester, diol or combination thereof comprising at least one pendent fluorene group or other conformationally locked aromatic group.

Suitable diacid, diester, and diol starting materials and monomers have been described in the art. In some embodiments, the starting materials and monomers comprise a substituted fluorene, i.e. wherein the aromatic rings of the fluorene comprise one or more substituents. Substituents can include halogen (e.g. fluorine), alkyl, substituted alkyl, aryl, substituted aryl, acyl, acyloxy, alkoxy, phenoxy, alkylamino, acylamido, and nitrogen-containing groups. Various substituted fluorene compounds are commercially available and others can be prepared by standard methods.

Suitable monofluorene starting materials may have the general structure:

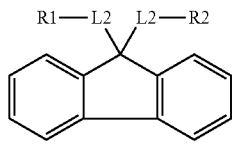

wherein L2 are independently a bond or a non-aromatic (e.g. divalent) linking group, and R1 and R2 are independently hydroxyl or a group comprising a carbonyl. In some embodiments, L2 is an alkylene group having no greater than 12, or 8, or 6, or 4 carbon atoms. In some favored embodiments, L2 is ethylene. In some embodiments, the starting material is a monofluorene diol, wherein R1 and R2 are OH. In other embodiments, R1 and R2 comprises a carbonyl group and may have the general formulas:

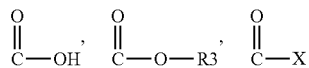

wherein R3 is an alkyl, aryl, ar alkaryl group that is optionally substituted and X is a halogen, such as chlorine.

Difluorene monomers typically comprise two fluorene groups bonded to a common (e.g. carbon) atom. The common carbon atom is present in the backbone of the polymerized polyester polymer.

Suitable difluorene starting materials may have the general structure:

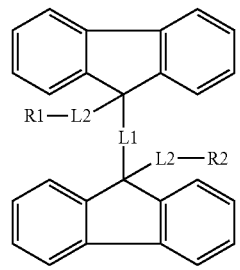

wherein L1 and L2 are independently a bond or a non-aromatic (e.g. divalent) linking group, and R1 and R2 are independently hydroxyl or a group comprising a carbonyl, as previously described.

In some embodiments, new fluorene monomers and polyester polymers prepared from such monomers are described. The new fluorene monomers are difluorene diols, difluorene methylene diesters, and difluorene methylene diacids. The aromatic rings of the fluorene group may optionally comprise substituents, as previously described.

In one embodiment, the difluorene monomer has the general formula:

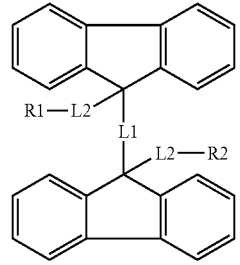

wherein R2 is OH and L1 and L2 are independently a bond or a non-aromatic linking groups. In some embodiments, L1 and L2 are C1-C4 alkylene groups. In some embodiments, the difluorene diol is difluorene ethane dipropanol or difluorene methane dipropanol.

In another embodiment, the difluorene monomer has the general formula:

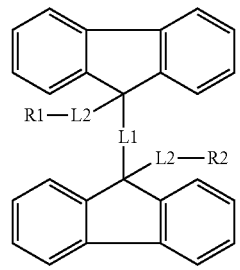

wherein L1 is methylene, L2 are independently a bond or a non-aromatic linking group, and R1 and R2 are independently hydroxyl or a group comprising a carbonyl, as previously described. In one embodiment, the difluorene monomer is difluorene methane dipropanionate ester.

The Tg of the fluorene monomer may be raised by the incorporation of a branched divalent linking group. This can be accomplished, for example, by use of methacylonitrile in place of acrylonitrile in the synthesis of the monomer.

In some favored embodiments, the polyester polymer is prepared from at least one glycol that comprises a pendent fluorene or other other conformationally locked aromatic group in combination with at least one diacid or diester monomer that also comprises a pendent fluorene or other conformationally locked aromatic group. This combination can provide a polyester polymer having a greater density of pendent aromatic rings per backbone atoms and the highest negative birefringence. In some embodiments, a monofluorene (e.g. diol) and a monofluorene (e.g. ester) are utilized. In this embodiment, the resulting polyester (e.g. homopolymer) may comprise up to about 0.25 aromatic rings per backbone atom and a negative birefringence up to about −0.035. In some embodiments, a monofluorene (e.g. diol) and a difluorene (e.g. ester) are utilized. In this embodiment, the resulting polyester (e,g, homopolymer) may comprise up to about 0.32 aromatic rings per backbone atom and a negative birefringence up to about −0.047. In another embodiment, a difluorene (e.g. ester) and difluorene diol are utilized. In this embodiment, the resulting polyesters (e.g. homopolymers) may comprise up to about 0.40 aromatic rings per backbone atom and a negative birefringence up to about −0.050 or −0.060. The previously described difluorene diol monomers are particularly useful for this embodiment.

In other embodiments, the polyester polymer is prepared from at least one diacid, diester, diol, or combination thereof, that comprises a pendent fluorene or other conformationally locked aromatic group in combination with another (e.g. non-fluorene) comonomer. As previously described, high negative birefringence can be obtained wherein at least 40% to 100 mol % of the units comprises at least one conformationally locked pendent aromatic (e.g. fluorene) group.

Various monomers for use in the synthesis of polyesters have been described in the art. The (e.g. non-fluorene) comonomer may be a diol, dicarboxylic acid or ester. Dicarboxylic acid comonomers include but are not limited to terephthalic acid, isophthalic acid, phthalic acid, all isomeric naphthalenedicarboxylic acids (2,6-, 1,2-, 1,3-, 1,4-, 1,5-, 1,6-, 1,7-, 1,8-, 2,3-, 2,4-, 2,5-, 2,8-), bibenzoic acids such as 4,4'-biphenyl dicarboxylic acid and its isomers, trans-4,4'-stilbene dicarboxylic acid and its isomers, 4,4'-diphenyl ether dicarboxylic acid and its isomers, 4,4'-diphenylsulfone dicarboxylic acid and its isomers, 4,4'-benzophenone dicarboxylic acid and its isomers, halogenated aromatic dicarboxylic acids such as 2-chloroterephthalic acid and 2,5-dichloroterephthalic acid, other substituted aromatic dicarboxylic acids such as tertiary butyl isophthalic acid and sodium sulfonated isophthalic acid, cycloalkane dicarboxylic acids such as 1,4-cyclohexanedicarboxylic acid and its isomers and 2,6-decahydronaphthalene dicarboxylic acid and its isomers, bi- or multi-cyclic dicarboxylic acids (such as the various isomeric norbornane and norbornene dicarboxylic acids, adamantane dicarboxylic acids, and bicyclo-octane dicarboxylic acids), alkane dicarboxylic acids (such as sebacic acid, adipic acid, oxalic acid, malonic acid, succinic acid, glutaric acid, azelaic acid, and dodecane dicarboxylic acid), and any of the isomeric dicarboxylic acids of the fused-ring aromatic hydrocarbons (such as indene, anthracene, pheneanthrene, benzonaphthene, fluorene and the like). Other aliphatic, aromatic, cycloalkane or cycloalkene dicarboxylic acids may be used. Alternatively, esters of any of these dicarboxylic acid monomers may be used in place of or in combination with the dicarboxylic acids themselves.

Suitable diol comonomers include but are not limited to linear or branched alkane diols or glycols (such as ethylene glycol, propanediols such as trimethylene glycol, butanediols such as tetramethylene glycol, pentanediols such as neopentyl glycol, hexanediols, 2,2,4-trimethyl-1,3-pentanediol and higher diols), ether glycols (such as diethylene glycol, triethylene glycol, and polyethylene glycol), chain-ester diols such as 3-hydroxy-2,2-dimethylpropyl-3-hydroxy-2,2-dimethylpropyl-3-hydroxy-2,2-d-i methyl propanoate, cycloalkane glycols such as 1,4-cyclohexanedimethanol and its isomers and 1,4-cyclohexanediol and its isomers, bi- or multicyclic diols (such as the various isomeric tricyclodecane dimethanols, norbornane dimethanols, norbornene dimethanols, and bicyclo-octane dimethanols), aromatic glycols (such as 1,4-benzenedimethanol and its isomers, 1,4-benzenediol and its isomers, bisphenols such as bisphenol A, 2,2'-dihydroxy biphenyl and its isomers, 4,4'-dihydroxymethyl biphenyl and its isomers, and 1,3-bis(2-hydroxyethoxy)benzene and its isomers), and lower alkyl ethers or diethers of these diols, such as dimethyl or diethyl diols. Other aliphatic, aromatic, cycloalkyl and cycloalkenyl diols may be used.

Preferred glycol monomer molecules for use in forming glycol subunits of the polyester or copolyester include C2-C4 glycols, i.e. ethylene glycol; propylene glycol; 1,4-butanediol and isomers thereof; and mixture thereof. In some embodiments, the polyester polymer described herein comprises at least 70 mol %, 75 mol %, 80 mol %, 85 mol %, 90 mol %, 95 mol %, or 100 mol % of C2-C4 glycol subunits. Typically ethylene subunits provide higher birefringence than butylene subunits. Hence, in some embodiments, the polyester polymer described herein comprises at least 75 mol %, 80 mol %, 85 mol %, 90 mol %, 95 mol %, or 100 mol % of ethylene subunits.

In some embodiments the glycols optionally comprise substituents to adjust the refractive index. For example, a fluorinated diol may be utilized to lower the refractive index. One suitable fluorinated diol comprises a nonafluorobutanesulfonamido group.

Tri- or polyfunctional comonomers, which can serve to impart a branched structure to the polyester molecules, can also be used. They may be of either the carboxylic acid, ester, hydroxy or ether types. Examples include, but are not limited to, trimellitic acid and its esters, trimethylol propane, and pentaerythritol.

Although various aromatic comonomers can be employed in the synthesis of the polyester polymers, in preferred embodiments there are at least twice as many pendent fluorene or other other conformationally locked aromatic groups as aromatic group in the backbone of the polyester polymer. Thus the ratio of pendent aromatic groups to backbone aromatic groups is at least 2:1, or 3:1, or 4:1, or 5:1. In some embodiments, the concentration of other aromatic (e.g. without pendent fluorene) comonomers is no greater than 35 mol %, 30 mol %, 25 mol %, 20 mol %, 15 mol %, 10 mol % or 5 mole %.

In some embodiments, the polyester polymer is prepared from at least one diacid, diester, or combination thereof that comprises a pendent fluorene or other conformationally locked aromatic group and a conventional glycol monomer (i.e. that lacks fluorene). When the diacid and/or diester are a monofluorene, the resulting polyester (e.g. homopolymer) may comprise up to about 0.20 aromatic rings per backbone atom and a negative birefringence up to about −0.025. When the diacid and/or diester are a difluorene, the resulting polyester (e.g. homopolymer) may comprise about 0.25 to about 0.31 aromatic rings per backbone atom and a negative birefringence up to about −0.031.

In other embodiments, the polyester polymer is prepared from at least one glycol that comprises a pendent fluorene or other conformationally locked aromatic group in combination with a conventional diacid or diester monomer (i.e. that lacks fluorene).

As the number of aromatic rings per backbone atom increases, the refractive index of the polyester polymer also increases. For example when the polyester polymer is a homopolymer comprising up to about 0.20 aromatic rings per backbone atom, the refractive index may range from 1.50 or 1.51 to 1.58 or 1.59 or 1.60. However, when the polyester polymer is a homopolymer comprising about 0.25 to 0.30 aromatic rings per backbone atom, the refractive index can be at least 1.61 or 1.62. Further, when the polyester polymer is a homopolymer comprising about 0.32 aromatic rings per backbone atoms, the refractive index can be at least 1.62; whereas when the polyester polymer is a homopolymer comprising greater than 0.32 to about 0.40 or greater aromatic rings per backbone atom the refractive index can range up to about 1.65, or greater.

In some embodiments, the polyester polymers described herein do not exhibit a DSC second scan crystallization peak and thus do not contain substantial amounts of crystallinity. Thus, such polyester polymer can be characterized as being amorphous.

The glass transition temperature (Tg) of the polyester polymers described herein, as measured according to the test method described in the examples, can range from about 50° C. to about 200° C. Preferred polyester polymers suitable for the manufacture of (e.g. multilayer or oriented) polyester optical films typically have a Tg of at least 60° C.

As the number of aromatic rings per backbone atom increases, the Tg of the polyester polymer also increases. For example when the polyester polymer is a homopolymer comprising two aromatic rings per repeat unit, the Tg of the polyester can range from 52° C. to about 70° C. However, when the polyester polymer is a homopolymer comprising four aromatic rings per repeat unit, the Tg of the polyester can ranges from about 90° C. to about 117° C. Further, when the polyester polymer is a homopolymer comprising six aromatic rings per repeat unit, the Tg can be at least about 125° C. However, when the polyester polymer is a homopolymer comprising eight aromatic rings per repeat unit the Tg can range can be greater than 125° C., ranging up up to 145° C. and greater.

The Tg of the polyester polymers described herein can be increased by blending the polymer with miscible high Tg polymers. Suitable high Tg aliphatic polyesters include for example high Tg aliphatic polyesters, such as commercially available from Eastman under the trade designation "Tritan"; polycarbonate/copolyester blends, such as commercially available from Eastman under the trade designation (SA115), polyamides, polyimides, polyetheretherketone ("PEEK"), polysulfones, and the like. The Tg of the polyester polymer can also be increased by modifying the starting monomers as previously described.

One way to express birefringence is with respect to the average in-plane birefringence (biaxial or constrained uniaxial or unconstrained uniaxial) after the film is formed, i.e. stretched near the glass transition temperature at a temperature range from 60° C. to 160° C. range. Another way to express birefringence is with respect to the in-plane stretch direction after the film is formed.

The optical layers lacking a negatively birefringent polymer can retain a relatively isotropic index of refraction, even when stretched. When the negatively birefringent polyester polymer described herein is blended with a posively birefringent polymer, the birefringence of the mixture may be positive, greater than zero. Often, the average in-plane (e.g. constrained uniaxial) birefringence of one layer type is less than about 0.04, and more preferably less than about 0.02 at 632.8 nm. In favored embodiments, the second optical layers comprise a polyester polymer as described herein having a negative birefringence, i.e. a birefringence of less than 0. The polyester polymers may exhibit a birefringence, ranging from slightly less than 0 (e.g. −0.005) to −0.060. In some embodiments, the negative birefringence ranges from at least −0.001, or −0.005, or −0.010 to about −0.060.

As the number of aromatic rings per backbone atom increases, the polyester polymer becomes increasingly negatively birefringent. For example when the polyester polymer is a homopolymer comprising two aromatic rings per repeat unit, the birefringence of the polyester can range from −0.010 to about −0.025. However, when the polyester polymer is a homopolymer comprising four aromatic rings per repeat unit, the birefringence of the polyester can range from −0.025 or −0.030 to about −0.040. Further, when the polyester polymer is a homopolymer comprising six aromatic rings per repeat unit, birefringence can range from about −0.040 to −0.047. However, when the polyester polymer is a homopolymer comprising eight aromatic rings per repeat unit the polyester polymer can be even more negative birefringent, ranging up to −0.055 or −0.056, −0.057, −0.058, −0.059 or −0.060.

The first optical layer typically exhibits an average in-plane (e.g. constrained) uniaxial birefringence higher that the second optical layer. In some embodiments, the birefringence of the first optical layer is at least 0.10, or 0.15, or 0.20, or greater. For other types of multilayer optical films, such as those utilized as a mirror film, the out-of-plane birefringence properties are of importance. The first optical layer can exhibit an average out-of-plane birefringence of at least 0.10, or 0.15, or 0.20. However, since the difference in birefriengence rather than the absolute birefringence is of importance, the first optical layer can have an even lower birefringence, yet be sufficiently different that the second optical layer.

The intrinsic viscosity of the copolyester of the first and polymeric material of the second optical layers as well as optional coextrudeable additional (e.g. skin) layers is related to the molecular weight (in the absence of branching monomers) of the polymer. Typically, the polyesters have an intrinsic viscosity of greater than about 0.4 dL/g. The intrinsic viscosity is between about 0.4 to 0.9 dL/g. In some embodiments, the intrinsic viscosity may be no greater than 0.6 dL/g. Intrinsic viscosity, for purposes of this disclosure, is measured in a 60/40 wt. % phenol/o-dichlorobenzene solvent at 30° C. unless otherwise indicated.

Furthermore, the first optical layers, second optical layers, and coextrudeable additional layers are chosen to have similar rheological properties (e.g., melt viscosities). Typically, the second optical layers and coextrudeable additional layers have a glass transition temperature, Tg, that is either below or no greater than about 40° C. above the glass transition temperature of the first optical layers. Preferably, the glass transition temperature of the second optical layers and the optional additional layers is below the glass transition temperature of the first optical layers.

The polyester materials described herein are thermally stable at processing temperatures ranging from 200° C.-280° C.

The first optical layers 12 may be made from a variety of known birefringent polymers, optionally comprising a small concentration of a fluorene monomer is improve intralayer adhesion.

Suitable polyester copolymers include copolymers of PEN (e.g., copolymers of 2,6-, 1,4-, 1,5-, 2,7-, and/or 2,3-naphthalene dicarboxylic acid, or esters thereof, with (a) terephthalic acid, or esters thereof, (b) isophthalic acid, or esters thereof, (c) phthalic acid, or esters thereof, (d) alkane glycols; (e) cycloalkane glycols (e.g., cyclohexane dimethanol diol); (f) alkane dicarboxylic acids; and/or (g) cycloalkane dicarboxylic acids (e.g., cyclohexane dicarboxylic acid)), and copolymers of polyalkylene terephthalates (copolymers of terephthalic acid, or esters thereof, with (a) naphthalene dicarboxylic acid, or esters thereof, (b) isophthalic acid, or esters thereof, (c) phthalic acid, or esters thereof, (d) alkane glycols; (e) cycloalkane glycols (e.g., cyclohexane dimethane diol); (f) alkane dicarboxylic acids; and/or (g) cycloalkane dicarboxylic acids (e.g., cyclohexane dicarboxylic acid)). The copolyesters described may also be a blend wherein at least one component is a polyester polymer and other component(s) are other polyesters or polycarbonates.

Referring again to FIG. 1, the multilayer film may optionally comprise one or more of the additional layers 18 laminated to or formed as a skin layer over at least one surface of stack 16 as illustrated in FIG. 1. Layers of the same or differing materials may be distributed within the stack, as well as on one or two of the major surfaces.

In some embodiments, the additional layers 18 typically do not significantly participate in the determination of optical properties of the multilayer polymer film 10, at least across the wavelength region of interest. The additional layers 18 are typically not birefringent or orientable. Such additional layers may protect the optical layers from damage, aid in the co-extrusion processing, and/or to enhance post-processing mechanical properties and/or provide greater mechanical strength to the stack.

Alternatively, the appearance and/or performance of multilayer film may be altered by including additional layers such as a skin layer on a major surface or an underskin layer contiguous with a skin layer within the stack of film layers.

Typically, when the additional layers 18 are used as skin layers there will be at least some surface reflection. If the multilayer polymer film 10 is to be a polarizer, the additional layers preferably have an index of refraction which is relatively low. This decreases the amount of surface reflection. If the multilayer polymer film 10 is to be a mirror, the additional layers 18 preferably have an index of refraction which is high, to increase the reflection of light.

When the additional layers 18 are found within the stack 16, there will typically be at least some polarization or reflection of light by the additional layers 18 in combination with the optical layers 12, 14 adjacent to the additional layers 18. Typically, however, the additional layers 18 have a thickness which dictates that light reflected by the additional layers 18 within the stack 16 has a wavelength outside the region of interest, for example, in the infrared region for visible light polarizers or mirrors.

The additional layers may be prepared from polyesters such as coPEN. The additional layers may also be prepared from any of the polymeric materials previously described for use as the second low refractive index layer.

Skin layers and interior layers may be integrated at the time of film formation, either by coextrusion or in a separate coating or extrusion step, or they may be applied to the finished film at a later time, such as by coating or lamination of a skin layer to a previously formed film. Total additional layer thicknesses typically range from about 2% to about 50% of the total thickness of multilayer film.

Examples of additional layers or coatings are described in U.S. Pat. Nos. 6,368,699, and 6,459,514 both entitled "Multilayer Polymer Film with Additional Coatings or Layers,", and U.S. Pat. No. 6,783,349 to Neavin et al., entitled "Apparatus for Making Multilayer Optical Films,".

The composition of additional layers may be chosen, for example, to protect the integrity of layers 12, 14 during or after processing, to add mechanical or physical properties to multilayer film 10; or to add optical functionality to multilayer film 10. Functional components such as antistatic additives, ultraviolet light absorbers (UVAs), hindered amine light stabilizers (HALS), dyes, colorants, pigments, antioxidants, slip agents, low adhesion materials, conductive materials, abrasion resistant materials, optical elements, dimensional stabilizers, adhesives, tackifiers, flame retardants, phosphorescent materials, fluorescent materials, nanoparticles, anti-graffiti agents, dew-resistant agents, load bearing agents, silicate resins, light diffusing materials, light absorptive materials and optical brighteners may be included in these layers, preferably such that they do not substantially interfere with the desired optical or other properties of the resulting product. In some exemplary embodiments, one or more additional layers may be or may include diffusers, such as a rough, matte or structured surface, a beaded diffuser or a diffuser including organic and/or inorganic particles, or any number or combination thereof.

One exemplary skin layer comprises a PMMA or polycarbonate/copolyester blend polymer (SA115) in combination with (e.g. about 2-3 wt-%) an ultraviolet light absorber such as 2-(4,6-diphenyl-1,3,5-triazin-2-yl)-5-(hexyloxy)-phenol), commercially available from Ciba under the trade designation "Tinuvin 1577"; (e.g. about 0.5 wt-%) of a hindered amine light stabilizer such as 10 wt % dimethyl succinate polymer with 4-hydroxy-2,2,6,6,-tetramethyl-1-piperidineethanol, 90 wt % N,N'''-[1,2-ethanediylbis[[[4,6-bis[butyl(1,2,2,6,6-pentamethyl-4-piperidinyl)amino]-1,3,5-traizin-2-yl]imino]-3,1-propanediyl]]bis[N'N''-dibutyl-N'N''-bis(1,2,2,6,6-pentamethyl-4-piperidinyl)]-1, commercially available from Ciba under the trade designation "Chimmasorb 119 FL", and (e.g. about 0.1 wt-%) of an antioxidant such as benzenepropanoic acid, 3,5-bis(1,1-dimethylethyl)-4-hydroxy-, 2,2-bis[[3-[3,5-bis(1,1-dimethylethyl)-4-hydroxyphenyl]-1-oxopropoxy]m, commercially available from Ciba under the trade designation "Irganox 1010 FF" or bis(2,4-di-tert-butylphenyl)pentaerythritol diphosphite, commercially available from Chemtura Corporation under the trade designation "Ultranox 626".

In one example, skin layers are used to aid in post-extrusion processing; for example, by preventing sticking of the film to hot rollers or tenter clips. In another embodiment, skin layers are added to impart desired barrier properties to multilayer film. For example, barrier films or coatings may be added as skin layers or as a component in skin layers to alter the transmissive properties of the multilayer film towards liquids, such as water or organic solvents, or gases, such as oxygen or carbon dioxide.

Skin layers may also be added to impart or improve abrasion resistance in the resulting multilayer film. For example, a skin layer comprising inorganic particles such as silica embedded in a polymer matrix may be used. In another embodiment, skin layers may comprise an abrasion resistant coating such as described in U.S. Pat. No. 5,677,050. Skin layers may also be added to impart or improve puncture and/or tear resistance in the resulting multilayer film. Puncture or tear resistant skin layers may be applied during the manufacturing process or later coated onto or laminated to multilayer film 10. Adhering these layers to multilayer film 10 during the manufacturing process, such as by a coextrusion process, provides the advantage that multilayer film 10 is protected during the manufacturing process.

In one example, additional layer(s) includes a dye or pigment that absorbs in one or more selected regions of the spectrum. Exemplary selected regions of the spectrum may include portions or all of the visible spectrum as well as ultraviolet and infrared. If all of the visible spectrum is absorbed, the layer will appear opaque. Materials for layers can be selected in order to change the apparent color of light transmitted or reflected by multilayer film. They can also be used to compliment the properties of the film, particularly where the film transmits some frequencies while reflecting others. In another embodiment, the use of a UV absorptive material in a skin cover layer is particularly desirable because it may be used to protect inner layers that may sometimes be unstable when exposed to UV radiation. In one embodiment, a fluorescent material is incorporated into the additional layer. Fluorescent materials absorb electromagnetic energy in the ultraviolet region of the spectrum and reemit in the visible.

Adhesives, including pressure sensitive adhesives, form another desirable class of materials that may be applied to a multilayer stack as a skin layer. Generally, pressure sensitive adhesives are applied when multilayer film is intended for later lamination to another material, such as a glass or metal substrate.

Another material that may be incorporated in skin layer is a slip agent. A slip agent will make multilayer film easier to handle during the manufacturing process. Typically a slip agent is used with a mirror film rather than a film intended to transmit a portion of the light striking it. The side including the slip agent is typically the side intended to be laminated to a supporting substrate in order to prevent the slip agent from increasing haze associated with the reflection.

Many of the advantages derived from skin layers can also be derived from an analogous internal layer. Thus, the foregoing discussion regarding skin layers is also applicable to internal layer(s).

Other additional layers include layers containing holographic images, holographic diffusers, or other diffusing layers. The foregoing has described examples of various layers that can be applied to a multilayer film stack to alter its properties. In general, any additional layers may be added, typically offering different mechanical, chemical, or optical properties than those of the layers 12, 14.

In the exemplary embodiment, the additional layer may be an absorbing or dichroic polarizer layer, as described, for example, in U.S. Pat. No. 6,096,375 to Ouderkirk et al., entitled "Optical Polarizer,". In some such configurations, the transmission axis of a dichroic polarizer is aligned with the transmission axis of a reflective polarizer.

A description of the process conditions and considerations for forming multilayer polymer films is found in WO99/36248 entitled "Process for Making Multilayer Optical Film."

The films are generally prepared by co-extruding the individual polymers to form multilayer film and then orienting film by stretching at a selected temperature, optionally followed by heat-setting at a selected temperature. Alternatively, the extrusion and orientation steps may be performed simultaneously. In the case of polarizers, the film is stretched substantially in one direction (uniaxial orientation), while in the case of mirror films, the film is stretched substantially in two directions (biaxial orientation), which may be performed simultaneously or sequentially.

In different processing embodiments, the multilayer film may be allowed to dimensionally relax in a cross-stretch direction, resulting in a natural reduction in cross-stretch (equal to the square root of the stretch ratio); the multilayer film may be constrained to limit any substantial change in cross-stretch dimension; or the multilayer film may be actively stretched in a cross-stretch dimension. For example, the multilayer film may be stretched in the machine direction, as with a length orienter, or in width using a tenter.

The pre-stretch temperature, stretch temperature, stretch rate, stretch ratio, heat set temperature, heat set time, heat set relaxation, and cross-stretch relaxation are selected to yield a multilayer film having the desired refractive index relationship and physical dimensions. These variables are interdependent; thus, for example, a relatively low stretch rate could be used if coupled with, for example, a relatively low stretch temperature. In general, a stretch ratio in the range from about 1:2 to about 1:10 (more preferably about 1:3 to about 1:7) in the stretch direction and from about 1:0.2 to about 1:10 (more preferably from about 1:0.5 to about 1:7) orthogonal to the stretch direction is selected in an exemplary embodiment.

Suitable multilayer films may also be prepared using techniques such as spin coating (e.g., as described in Boese et al., J. Polym. Sci.: Part B, 30:1321 (1992) for birefringent polyimides) and vacuum deposition (e.g., as described by Zang et. al., Appl. Phys. Letters, 59:823 (1991) for crystalline organic compounds); the latter technique is particularly useful for certain combinations of crystalline organic compounds and inorganic materials.

EXAMPLES

Materials List

| Material | Source |
| --- | --- |
| Fluorene | Alfa Aesar (Ward Hill, MA) |
| Acrylonitrile | Alfa Aesar (Ward Hill, MA) |
| 1,4-Dioxane | Alfa Aesar (Ward Hill, MA) |
| Potassium tert-butoxide | Alfa Aesar (Ward Hill, MA) |
| Paraformaldehyde | VWR Scientific (Radnor, PA) |
| Benzyltrimethylammonium hydroxide (TRITON B) | Alfa Aesar (Ward Hill, MA) |
| Sulfuric acid | Alfa Aesar (Ward Hill, MA) |
| 6N HCL solution | Alfa Aesar (Ward Hill, MA) |
| Ethyl alcohol | PHARMCO-AAPER (Shelbyville, KY) |
| 1,4-Butanediol | Sigma-Aldrich (St. Louis, MO) |
| Potassium hydroxide (KOH) | VWR Scientific (Radnor, PA) |
| Toluene | EMD Chemicals (Gibbstown, NJ) |
| Tetrahydrofuran (THF) | EMD Chemicals (Gibbstown, NJ) |
| Diethyl ether ("ether") | EMD Chemicals (Gibbstown, NJ) |
| Ethyl acetate | EMD Chemicals (Gibbstown, NJ) |
| Dimethyl formamide (DMF) | EMD Chemicals (Gibbstown, NJ) |
| Methylene chloride | EMD Chemicals (Gibbstown, NJ) |
| Ethylene glycol (EG) (only used in PETN80 preparation) | MEGlobal Americas Inc. (Midland, MI) |
| Ethylene glycol (EG) (all other Examples) | Mallinckrodt Baker Inc. (Phillipsburg, NJ) |
| 1,1,2,2,3,3,4,4,4-Nonafluoro-N,N-bis(2-hydroxyethyl)butane-1-sulfonamide | Prepared at 3M (St. Paul, MN) by method given below* |
| Succinic acid | Sigma-Aldrich (St. Louis, MO) |
| Lithium Aluminun Hydride (LiAlH, or LAH) | Sigma-Aldrich (St. Louis, MO) |
| Hexanoyl chloride | Sigma-Aldrich (St. Louis, MO) |
| Titanium tetrabutoxide | E.I. DuPont de Nemours (Wilmington, DE) |
| CELITE | Sigma-Aldrich (St. Louis, MO) |
| Dimethyl terephthalate (DMT); | Invista (Wilmington, NC) |
| Dimethyl 2,6-napthalenedicarboxylate (DM-2,6-NDC); | BP Chemicals (Naperville, IL) |
| Trimethylolpropane (TMP) | Celanese Canada, Inc (Edmonton, AB, Canada) |
| Antimony triacetate | Arkema Chemicals Ltd. (Philadelphia, PA) |
| Zinc acetate | Spectrum Chemicals (Gardena, CA) |
| Sodium acetate | Alfa Aesar (Ward Hill, MA) |
| Cobalt acetate | Shepherd Chemical (Norwood, OH) |
| Triethyl phosphono acetate | Phosphate Products (Cranbury, NJ) |

*1,1,2,2,3,3,4,4,4-Nonafluoro-N,N-bis(2-hydroxyethyl)butane-1-sulfonamide was prepared according to procedures given in "Hydroxyalkylation of perfluoroalkanesulfonamides" by Niederpruem, Hans, et al., in *Justus Liebigs Annalen der Chemie* 1973, (1), 11-19.

Monomer Synthesis Examples

Examples 1a-1d

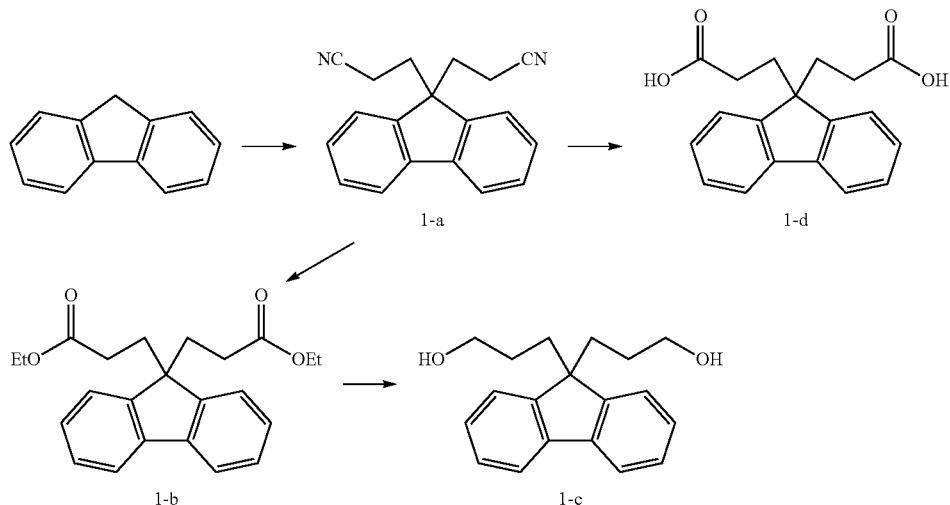

Example 1a

3-[9-(2-Cyanoethyl)-9H-fluoren-9-yl]-propionitrile (1-a) was prepared following the procedure described in *J. Am. Chem. Soc.* 1942, 64, 2457-2459.

Example 1b

3-[9-(2-Ethoxycarbonyl-ethyl)-9H-fluoren-9-yl]-propionic acid ethyl ester (1-b) was prepared following the procedures described in *J. Org. Chem.* 1961, 26, 3280-3287 and German Patent DE 1941227, 1968 (Union Carbide).

Example 1c

3-[9-(3-Hydroxy-propyl)-9H-fluoren-9-yl]-propan-1-ol (1-c)

A 2-neck 1-Liter round bottom flask was equipped with a condenser, a magnetic stir bar and an addition funnel. The flask was charged with 15 mL of anhydrous THF and 30 mL of anhydrous ether. Lithium aluminum hydride (4.80 g) was then carefully added to the flask. 3-[9-(2-Ethoxycarbonyl-ethyl)-9H-fluoren-9-yl]-propionic acid ethyl ester (18.2 g) was dissolved in 95 mL of anhydrous ether and 37 mL of anhydrous THF and this mixture was added to the addition funnel. The solution of diester was then added dropwise to the rapidly stirred lithium aluminum hydride suspension over a period of 60 min. After an additional 2 hours, the rapidly stirred reaction mixture was carefully treated by the dropwise addition of water (31 mL), followed by 35% NaOH solution (63 mL), and finally more water (66 mL). Additional diethyl ether was added to keep the slurry stirring. After stirring for 30 min, the ether/THF layer was allowed to separate and was then decanted from the aluminum salts. The salts were rinsed with additional portions of diethyl ether. The combined organic portions were concentrated under reduced pressure to give a white solid. The white solid was dissolved in 200 mL of ether and 100 mL of THF, washed with 1N HCl solution (2×75 mL) and brine. The organic layer was dried over MgSO$_4$, filtered and concentrated under reduced pressure. The resulting white solid was crystallized from hot toluene to give the title compound (1-c) (12.3 g) as white flakes. $^1$H NMR (CDCl$_3$, 500 MHz) δ 7.71 (m, 2H), 7.37-7.27 (m, 6H), 3.32 (t, J=6.4 Hz, 4H), 2.09 (m, 4H), 0.87 (m, 4H).

Example 1d

3-[9-(2-Carboxy-ethyl)-9H-fluoren-9-yl]-propionic acid (1-d)) was prepared following the procedure described in *J. Am. Chem. Soc.* 1942, 64, 2457-2459.

Examples 2a-2d

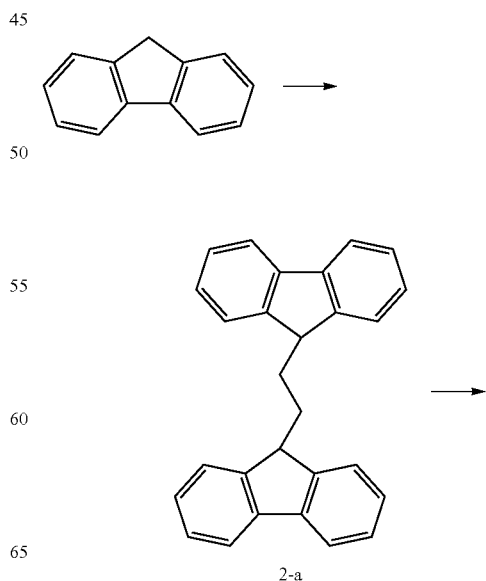

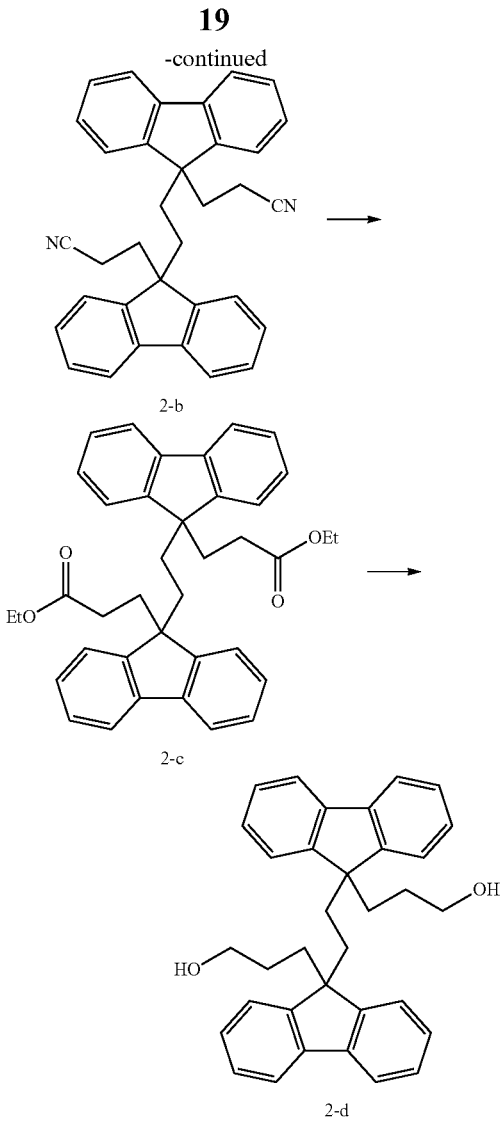

Examples 2a and 2b 1,2-Bis(9-fluorenyl)ethane (2-a) and 3-(9-[2-[9-(2-Cyanoethyl)-9H-fluoren-9-yl]-ethyl]-9H-fluoren-9-yl)-propionitrile (2-b) were prepared following the procedures described in *J. Org. Chem.* 1965, 30, 2540-2542 and U.S. Pat. No. 3,426,069, 1969 (Union Carbide).

Example 2c 3-(9-{2-[9-(2-Ethoxycarbonyl-ethyl)-9H-fluoren-9-yl]-ethyl}-9H-fluoren-9-yl)-propionic acid ethyl ester (2-c)

A 3-neck 1-Liter round bottom flask was equipped with a $N_2$ inlet, a condenser and a magnetic stir bar. The flask was charged with 3-(9-{2-[9-(2-cyanoethyl)-9H-fluoren-9-yl]-ethyl}-9H-fluoren-9-yl)-propionitrile (94 g), 350 ml of absolute ethanol and 78 ml of concentrated sulfuric acid. The mixture was heated to reflux and stirred overnight. After the reaction mixture was cooled to room temperature, the solid precipitate was removed by filtration and washed with ethanol twice. The solid was crystallized from hot ethanol to give the title compound (2-c) (70 g) as white crystals. $^1$H NMR (CDCl$_3$, 300 MHz) δ 7.73 (d, J=7.1 Hz, 4H), 7.37 (m, 4H), 7.28 (m, 4H), 6.98 (d, J=7.4 Hz, 4H), 3.82 (quartet, J=7.3 Hz, 4H), 1.94 (m, 4H), 1.35 (m, 4H), 1.25 (s, 4H), 1.02 (t, J=7.3 Hz, 6H).

Example 2d 3-(9-{2-[9-(3-Hydroxy-propyl)-9H-fluoren-9-yl]-ethyl}-9H-fluoren-9-yl)-propan-1-ol (2-d)

A 2-neck 1-Liter round bottom flask was equipped with a condenser, a magnetic stir bar and an addition funnel. The flask was charged with 100 mL of anhydrous ether. Lithium aluminum hydride (2.30 g) was then carefully added to the flask. 3-(9-{2-[9-(2-Ethoxycarbonyl-ethyl)-9H-fluoren-9-yl]-ethyl}-9H-fluoren-9-yl)-propionic acid ethyl ester (11.3 g, 20.2 mmol) was suspended in 100 mL of anhydrous ether and added to the addition funnel. The suspension of diester was then added dropwise to the rapidly stirred lithium aluminum hydride suspension. The addition funnel was rinsed with additional portions of anhydrous ether to rinse all of the diester into the reaction flask. The reaction mixture was then refluxed for several hours and then left at ambient temperature overnight. The rapidly stirred reaction mixture was carefully treated by the dropwise addition of water (2.3 mL), followed by 15% NaOH solution (2.3 mL), and finally more water (6.9 mL). After stirring for 2 h, the ether solution was filtered from the aluminum salts. The salts were rinsed with additional portions of diethyl ether. The combined organic portions were concentrated under reduced pressure to give a white solid. The white solid was dissolved in 100 mL of ethyl acetate, washed with 1N HCl solution, water, and brine. The organic layer was dried over Na$_2$SO$_4$, filtered, and concentrated under reduced pressure. The resulting white solid was crystallized from hot toluene to give the title compound (2-d) (8.8 g) as white crystals. $^1$H NMR (CDCl$_3$, 500 MHz) δ 7.73 (d, J=7.5 Hz, 4H), 7.36 (m, 4H), 7.28 (m, 4H), 7.00 (d, J=7.5 Hz, 4H), 3.15 (t, J=6.7 Hz, 4H), 1.65 (m, 4H), 1.24 (s, 4H), 0.64 (m, 4H).

Examples 3a-3d

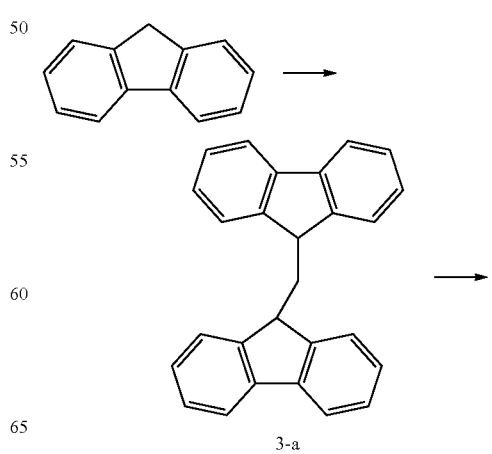

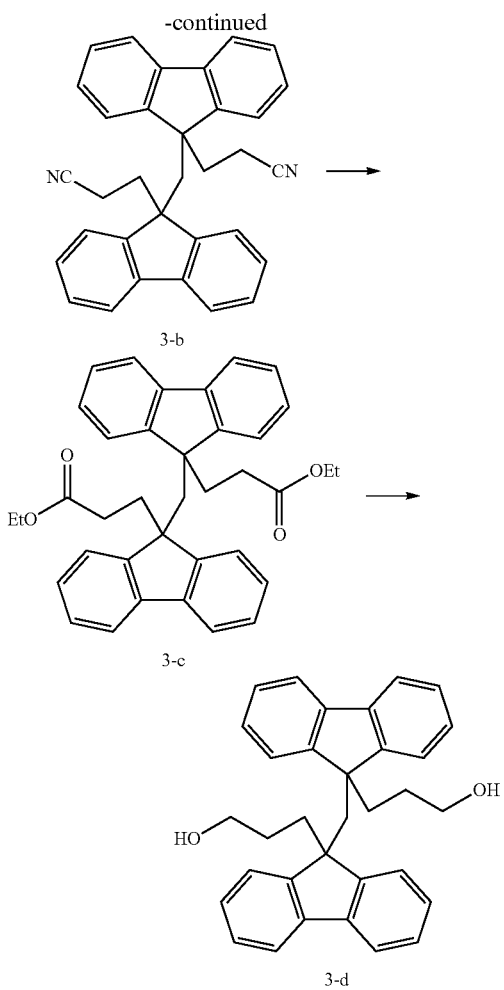

Example 3a 1,2-Bis(9-fluorenyl)methane (3-a) was prepared following the procedure described in *J. Am. Chem. Soc.* 2003, 125, 8712-8713.

Example 3b

3-{9-[9-(2-Cyanoethyl)-9H-fluoren-9-ylmethyl]-9H-fluoren-9-yl}-propionitrile (3-b)

A 3-neck 5-Liter round bottom flask was equipped with a condenser, a nitrogen inlet, and a mechanical stirrer. The flask was then charged with 1,2-bis(9-fluorenyl)methane (728.8 g) and 3.8 L of 1,4-dioxane. TRITON B (36.4 g, 40% aqueous solution) was then added followed by the drop wise addition of acrylonitrile (269.5 g) at a rate that kept the reaction temperature below 40° C. The reaction was then stirred at ambient temperature overnight. The reaction mixture was then treated with an additional 30.0 g of acrylonitrile and stirring was continued for 2 h followed by heating to 40° C. for 30 min. The reaction mixture was then cooled to room temperature and the solid was isolated by filtration. The resulting solid was crystallized from a mixture of toluene and ethanol to give 626.5 g of the title compound (3-b). $^1$H NMR (CDCl$_3$, 300 MHz) δ 7.09-7.00 (m, 8H), 6.88 (m, 4H), 6.79 (d, J=7.4 Hz, 4H), 3.08 (s, 2H), 2.29 (m, 4H), 1.09 (m, 4H).

Example 3c

3-{9-[9-(2-Ethoxycarbonylethyl)-9H-fluoren-9-ylmethyl]-9H-fluoren-9-yl}-propionic acid ethyl ester (3-c)

A 3-neck 5-Liter round bottom flask was equipped with a condenser, a nitrogen inlet, and a mechanical stirrer. The flask was charged with 3-{9-[9-(2-Cyanoethyl)-9H-fluoren-9-ylmethyl]-9H-fluoren-9-yl}-propionitrile (520.4 g) and 2.8 L of absolute ethanol. Sulfuric acid (585 mL) was then carefully added to the reaction mixture. The mixture was then heated to reflux overnight. The reaction mixture was cooled to ambient temperature and the resulting solid was isolated by filtration. The solid was crystallized from ethanol, washed with three portions of hot water, and then dried under vacuum at 70° C. to give 335.6 g of the title compound (3-c). $^1$H NMR (CDCl$_3$, 300 MHz) δ 7.04 (m, 4H), 6.98 (m, 4H), 6.85-6.75 (m, 4H), 3.85 (quartet, J=7.2 Hz, 4H), 3.13 (s, 2H), 2.24 (m, 4H), 1.18 (m, 4H), 1.03 (t, J=7.2 Hz, 6H).

Example 3d

3-{9-[9-(3-Hydroxypropyl)-9H-fluoren-9-ylmethyl]-9H-fluoren-9-yl}-propan-1-ol (3-d)

3-{9-[9-(2-Ethoxycarbonylethyl)-9H-fluoren-9-ylmethyl]-9H-fluoren-9-yl}-propionic acid ethyl ester (9.7 g) was dissolved in 200 mL of THF and treated with lithium aluminum hydride (1.97 g) at 0° C. under an atmosphere of nitrogen. After stirring overnight, the reaction mixture was treated with 2.0 mL of water followed by 2.0 mL of 15% NaOH solution and then 6.0 mL of water. The reaction mixture was filtered through a pad of CELITE, rinsing with ethyl acetate. The filtrate was washed with 1N HCl solution, water (2×) and brine. The organic portion was dried over Na$_2$SO$_4$, filtered, and concentrated under reduced pressure to give a white solid. The white solid was crystallized from toluene to give 5.85 g of the title compound as white crystals. $^1$H NMR (CDCl$_3$, 500 MHz) δ 7.04 (m, 4H), 6.98 (m, 4H), 6.83-6.77 (m, 4H), 3.19 (t, J=6.4 Hz, 4H), 3.09 (s, 2H), 1.94 (m, 4H), 1.00 (br s, 2H), 0.47 (m, 4H).

Example 4

2-(9H-Fluoren-9-yl)-succinic acid (4-a)

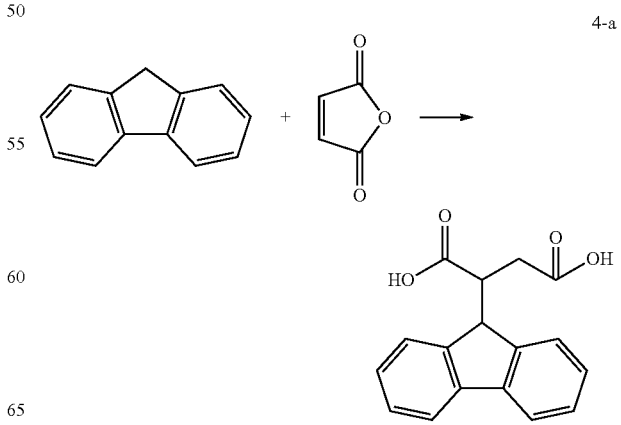

2-(9H-Fluoren-9-yl)-succinic acid (4-a) was prepared following the procedure described in *J. Am. Chem. Soc.*, 1949, 71 (6), 1917-1918.

The resulting monomer comprises a pendent fluorene group. However, the pendent fluorene is not conformationally locked.

Examples 5a-5d

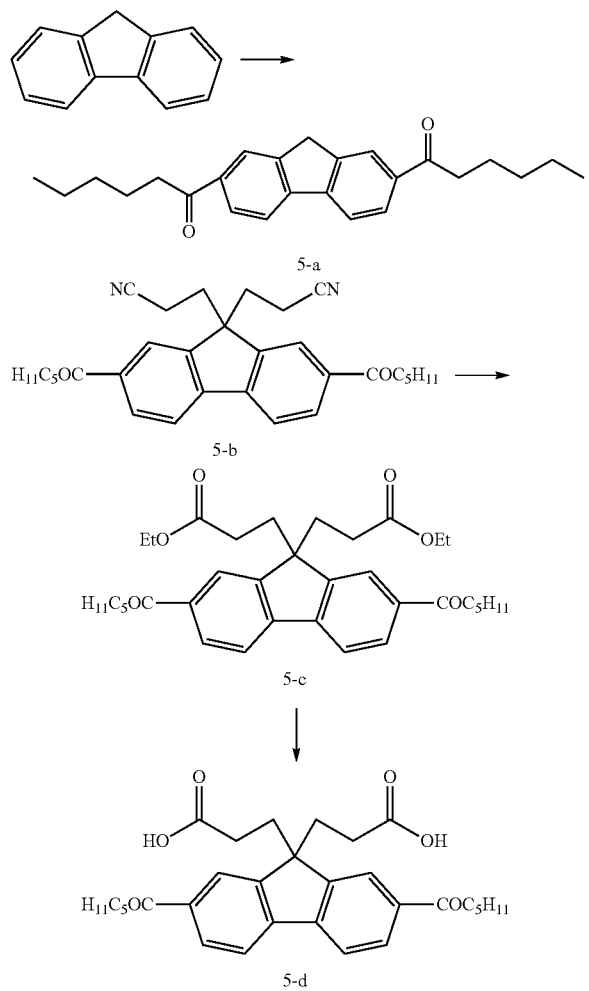

Example 5a 1-(7-Hexanoyl-9H-fluoren-2-yl)-hexan-1-one (5-a) can be prepared following the procedure described in *J. Chem. Soc., Chem. Commun.* 2004, 144-145.

Example 5b

3-[9-(2-Cyano-ethyl)-2,7-dihexanoyl-9H-fluoren-9-yl]-propionitrile (5-b)

A 3-neck 250-mL round bottom flask was equipped with a condenser, a nitrogen inlet, an addition funnel, and a magnetic stir bar. The flask was then charged with 14.50 g of 1-(7-hexanoyl-9H-fluoren-2-yl)-hexan-1-one and 80 mL of methylene chloride. TRITON B (0.80 g, 40% methanol solution) was then added, followed by the drop wise addition of acrylonitrile (4.67 g) at a rate that kept the reaction temperature below 35° C. The reaction was then stirred at ambient temperature for three hours. The solvent was then removed under reduced pressure and the resulting solid was crystallized from ethanol to give 12.60 g of the title compound. $^1$H NMR (CDCl$_3$, 300 MHz) δ 8.11-8.03 (m, 4H), 7.89 (m, 2H), 3.04 (m, 4H), 2.55 (m, 4H), 1.81 (m, 4H), 1.56 (m, 4H), 1.44-1.38 (m, 8H), 0.94 (m, 6H).

Example 5c

3-[9-(2-Ethoxycarbonyl-ethyl)-2,7-dihexanoyl-9H-fluoren-9-yl]-propionic acid ethyl ester (5-c)

A 2-neck 100-mL round bottom flask was equipped with a condenser, a nitrogen inlet, and a magnetic stirrer. The flask was charged with 3-[9-(2-cyano-ethyl)-2,7-dihexanoyl-9H-fluoren-9-yl]-propionitrile (11.80 g) and 45 mL of absolute ethanol. Sulfuric acid (20.0) was then carefully added to the reaction mixture. The mixture was then heated to reflux overnight. The reaction mixture was cooled to about −20° C. and the resulting solid was isolated by filtration. The solid was washed with three portions of ethanol and three portions of water and then dried under vacuum at 70° C. to give 11.5 g of the title compound. $^1$H NMR (CDCl$_3$, 300 MHz) δ 8.04-7.99 (m, 4H), 7.83 (m, 2H), 3.90 (quartet, J=7.2 Hz, 4H), 3.02 (t, J=7.5 Hz, 4H), 2.50 (m, 4H), 1.78 (m, 4H), 1.52 (m, 4H), 1.43-1.37 (m, 8H), 1.10 (t, J=7.2 Hz, 6H), 0.94 (m, 6H).

Example 5d

3-[9-(2-Carboxy-ethyl)-2,7-dihexanoyl-9H-fluoren-9-yl]-propionic acid (5-d)

A 2-neck 250-mL round bottom flask was equipped with a condenser, a nitrogen inlet, and a magnetic stirrer. The flask was charged with 3-[9-(2-ethoxycarbonyl-ethyl)-2,7-dihexanoyl-9H-fluoren-9-yl]-propionic acid ethyl ester (10.76 g), 100 mL of water and 5.0 g of sodium hydroxide. The mixture was then heated to reflux overnight. The reaction mixture was cooled to ambient temperature and acidified to pH=1 by addition of 6N hydrochloric acid solution. The resulting solid was isolated by filtration and washed with three portions of water. The solid was dried under vacuum at 70° C. to give 8.5 g of the title compound. $^1$H NMR (CDCl$_3$, 300 MHz) δ 8.02-7.98 (m, 4H), 7.82 (m, 2H), 2.99 (t, J=7.6 Hz, 4H), 2.47 (m, 4H), 1.74 (m, 4H), 1.53 (m, 4H), 1.40-1.34 (m, 8H), 0.91 (m, 6H).

Polymer Synthesis Examples

Example 6

A 3-neck 100-mL round bottom flask equipped with N$_2$ inlet, distillation apparatus, and mechanical stir bar was charged with 8.3706 g 3-[9-(2-Ethoxycarbonyl-ethyl)-9H-fluoren-9-yl]-propionic acid ethyl ester, 3.5445 g of ethylene glycol, 4.2 mg of zinc acetate, and 4.0 mg of titanium tetrabutoxide. The mixture was heated to 220° C., gradually producing ethanol distillate. The reaction was kept at 220~250° C. for three hours to complete the transesterification reaction. Vacuum was applied gradually over about 30 min to full vacuum (~0.4 mmHg). The temperature was raised to 250~255° C. and held for two and a half hours with melt viscosity increasing during the polymerization. The reaction was stopped and polymer was obtained.

Example 7

Poly(butylene 3-[9-(2-Ethoxycarbonyl-ethyl)-9H-fluoren-9-yl]-propionate)

A 3-neck 100-mL round bottom flask equipped with $N_2$ inlet, distillation apparatus, and mechanical stir bar was charged with 3.551 g 3-[9-(2-Carboxy-ethyl)-9H-fluoren-9-yl]-propionic acid and 2.4748 g of 1,4-butanediol. The mixture was heated to 230° C., gradually producing water distillate. The reaction was kept at 230~250° C. for about two hours to complete the transesterification reaction. 2.0 mg of antimony triacetate was charged. Vacuum was applied gradually over about 30 min to full vacuum (~0.3 mmHg). The temperature was raised to 250~260° C. and held for three hours with melt viscosity increasing during the polymerization. The reaction was stopped and polymer was obtained. Intrinsic viscosity was measured using methods typical for polyesters, using a 60/40 wt-% mixture of phenol and o-dichlorobenzene as the solvent, at 30 C. Intrinsic viscosity was 0.485 dL/g

Example 8

A 3-neck 100-mL round bottom flask equipped with $N_2$ inlet, distillation apparatus, and mechanical stir bar was charged with 2.4968 g 3-[9-(2-Carboxy-ethyl)-9H-fluoren-9-yl]-propionic acid and 6.8535 g of 1,1,2,2,3,3,4,4,4-nonafluoro-N,N-bis(2-hydroxyethyl)butane-1-sulfonamide. The mixture was heated to 220° C., gradually producing water distillate. The reaction was kept at 220~250° C. for about two and a half hours to complete the transesterification reaction. 2.0 mg of antimony triacetate was charged. Vacuum was applied gradually over about 30 min to full vacuum (~0.2 mmHg). The temperature was raised to 250~260° C. and held for three hours with melt viscosity increasing during the polymerization. The reaction was stopped and polymer was obtained.

Example 9

A 3-neck 100-mL round bottom flask equipped with $N_2$ inlet, distillation apparatus, and mechanical stir bar was charged with 2.9105 g 3-[9-(2-Ethoxycarbonyl-ethyl)-9H-fluoren-9-yl]-propionic acid ethyl ester, 2.1307 g of 3-[9-(3-Hydroxy-propyl)-9H-fluoren-9-yl]-propan-1-ol, 0.7888 g of ethylene glycol and 2.0 mg of titanium tetrabutoxide. The mixture was heated to 215° C., gradually producing ethanol distillate. The reaction was kept at 215~235° C. for two hours to complete the transesterification reaction. Vacuum was applied gradually over about 30 min to full vacuum (~0.4 mmHg). The temperature was raised to 235~245° C., and held for one and a half hour with melt viscosity increasing during the polymerization. The reaction was stopped and polymer was obtained.

Example 10

A 3-neck 100-mL round bottom flask equipped with $N_2$ inlet, distillation apparatus, and mechanical stir bar was charged with 5.6939 g 3-(9-{2-[9-(2-Ethoxycarbonyl-ethyl)-9H-fluoren-9-yl]-ethyl}-9H-fluoren-9-yl)-propionic acid ethyl ester, 1.5181 g of ethylene glycol, 5.6 mg of zinc acetate, and 2.8 mg of titanium tetrabutoxide. The mixture was heated to 205° C., gradually producing ethanol distillate. The reaction was kept at 205~240° C. for two and a half hours to complete the transesterification reaction. Vacuum was applied gradually over about 30 min to full vacuum (~0.7 mmHg). The temperature was raised to 245~255° C., and held for two hours, with melt viscosity increasing during the polymerization. The reaction was stopped and polymer was obtained.

Example 11

A 3-neck 100-mL round bottom flask equipped with $N_2$ inlet, distillation apparatus, and mechanical stir bar was charged with 4.776 g 3-(9-{2-[9-(2-Ethoxycarbonyl-ethyl)-9H-fluoren-9-yl]-ethyl}-9H-fluoren-9-yl)-propionic acid ethyl ester, 1.8489 g of 1,4-butanediol, and 2.4 mg of zinc acetate. The mixture was heated to 230° C., gradually producing ethanol distillate. The reaction was kept at 230~250° C. for two hours to complete the transesterification reaction. Vacuum was applied gradually over about 30 min to full vacuum (~0.8 mmHg). The temperature was raised to 250~255° C., and held for two and a half hours, with melt viscosity increasing during the polymerization. The reaction was stopped and polymer was obtained.

Example 12

A 3-neck 100-mL round bottom flask equipped with $N_2$ inlet, distillation apparatus, and mechanical stir bar was charged with 3.9329 g 3-(9-{2-[9-(2-Ethoxycarbonyl-ethyl)-9H-fluoren-9-yl]-ethyl}-9H-fluoren-9-yl)-propionic acid ethyl ester, 1.9480 g of 3-[9-(3-Hydroxy-propyl)-9H-fluoren-9-yl]-propan-1-ol, 0.6554 g of ethylene glycol, 5.6 mg of zinc acetate, and 2.8 mg of titanium tetrabutoxide. The mixture was heated to 220° C., gradually producing ethanol distillate. The reaction was kept at 220~240° C. for two hours to complete the transesterification reaction. Vacuum was applied gradually over about 30 min to full vacuum (~0.7 mmHg). The temperature was raised to 245~255° C., and held one and a half hours, with melt viscosity increasing during the polymerization. The reaction was stopped and polymer was obtained.

Example 13

A 3-neck 100-mL round bottom flask equipped with $N_2$ inlet, distillation apparatus, and mechanical stir bar was charged with 2.741 g 3-(9-{2-[9-(2-Ethoxycarbonyl-ethyl)-9H-fluoren-9-yl]-ethyl}-9H-fluoren-9-yl)-propionic acid ethyl ester, 2.2820 g of 3-(9-{2-[9-(3-Hydroxy-propyl)-9H-fluoren-9-yl]-ethyl}-9H-fluoren-9-yl)-propan-1-ol, 0.4263 g of ethylene glycol, 1.4 mg of zinc acetate, and 2.0 mg of titanium tetrabutoxide. The mixture was heated to 230° C., gradually producing ethanol distillate. The reaction was kept at 230~250° C. for two and a half hours to complete the transesterification reaction. Vacuum was applied gradually over about 30 min to full vacuum (~0.7 mmHg). The temperature was raised to 250~255° C., and held for one and a half hours, with melt viscosity increasing during the polymerization. The reaction was stopped and polymer was obtained.

Polymer was placed in a non-stick pan and placed in a vacuum oven at room temperature. The vacuum oven was reduced to a vacuum below 1 mmHg, and the temperature of the oven was then increased gradually to 200° C. over 3 hrs. The specimen was finally held at 200° C. and 0.5 mmHg for 48 hours. After the oven was cooled to room temperature, the specimen was removed.

Example 14

A 3-neck 100-mL round bottom flask equipped with $N_2$ inlet, distillation apparatus, and mechanical stir bar was charged with 4.8387 g 3-{9-[9-(2-Ethoxycarbonylethyl)-9H-fluoren-9-ylmethyl]-9H-fluoren-9-yl}-propionic acid ethyl ester, 1.3233 g of ethylene glycol, 2.4 mg of zinc acetate, and 2.8 mg of titanium tetrabutoxide. The mixture was heated to 220° C., gradually producing ethanol distillate. The reaction was kept at 220~240° C. for two hours to complete the transesterification reaction. Vacuum was applied gradually over about 30 min to full vacuum (~0.4 mmHg). The temperature was raised to 245~255° C., and held for one and half hours, with melt viscosity increasing during the polymerization. The reaction was stopped and polymer was obtained.

Polymer was placed in a non-stick pan and placed in a vacuum oven at room temperature. The vacuum oven was reduced to a vacuum below 1 mmHg, and the temperature of the oven was then increased gradually to 200° C. over 3 hrs. The specimen was finally held at 200° C. and 0.5 mmHg for 48 hours. After the oven was cooled to room temperature, the specimen was removed.

Example 15

A 3-neck 100-mL round bottom flask equipped with $N_2$ inlet, distillation apparatus, and mechanical stir bar was charged with 4.0006 g 3-{9-[9-(2-Ethoxycarbonylethyl)-9H-fluoren-9-ylmethyl]-9H-fluoren-9-yl}-propionic acid ethyl ester, 1.5885 g of 1,4-butanediol, and 2.0 mg of titanium tetrabutoxide. The mixture was heated to 200° C., gradually producing ethanol distillate. The reaction was kept at 200~235° C. for two and a half hours to complete the transesterification reaction. Vacuum was applied gradually over about 30 min to full vacuum (~0.3 mmHg). The temperature was raised to 240~250° C., and held for one and a half hours, with melt viscosity increasing during the polymerization. The reaction was stopped and polymer was obtained.

Polymer was placed in a non-stick pan and placed in a vacuum oven at room temperature. The vacuum oven was reduced to a vacuum below 1 mmHg, and the temperature of the oven was then increased gradually to 200° C. over 3 hrs. The specimen was finally held at 200° C. and 0.5 mmHg for 48 hours. After the oven was cooled to room temperature, the specimen was removed.

Example 16

A 3-neck 100-mL round bottom flask equipped with $N_2$ inlet, distillation apparatus, and mechanical stir bar was charged with 2.4813 g 3-{9-[9-(2-Ethoxycarbonylethyl)-9H-fluoren-9-ylmethyl]-9H-fluoren-9-yl}-propionic acid ethyl ester, 2.9878 g of 3-{9-[9-(3-Hydroxypropyl)-9H-fluoren-9-ylmethyl]-9H-fluoren-9-yl}-propan-1-ol, 0.5747 g of 1,4-butanediol, and 1.5 mg of titanium tetrabutoxide. The mixture was heated to 220° C., gradually producing ethanol distillate. The reaction was kept at 220~250° C. for two and a half hours to complete the transesterification reaction. Vacuum was applied gradually over about 30 min to full vacuum (~0.3 mmHg). The temperature was raised to ~250° C., and held for three hours, with melt viscosity increasing during the polymerization. The reaction was stopped and polymer was obtained.

Example 17

A 3-neck 100-mL round bottom flask equipped with $N_2$ inlet, distillation apparatus, and mechanical stir bar was charged with 3.4584 g 2-(9H-Fluoren-9-yl)-succinic acid and 2.6482 g of 1,4-butanediol. The mixture was heated to 215° C., gradually producing water distillate. The reaction was kept at 215~250° C. for about two hours to complete the transesterification reaction. 2.0 mg of antimony triacetate was charged. Vacuum was applied gradually over about 15 min to full vacuum (~0.3 mmHg). The temperature was raised to 250~260° C., and held for two and a half hours, with melt viscosity increasing during the polymerization. The reaction was stopped and polymer was obtained.

Example 18

A 3-neck 100-mL round bottom flask equipped with $N_2$ inlet, distillation apparatus, and mechanical stir bar was charged with 2.8258 g 3-(9-Ethoxycarbonylmethyl-2,7-di-hexanoyl-9H-fluoren-9-yl)-propionic acid, 1.4963 g of 3-[9-(3-Hydroxy-propyl)-9H-fluoren-9-yl]-propan-1-ol, and 0.7073 g of 1,4-butanediol. The mixture was heated to 235° C., gradually producing water distillate. The reaction was kept at 235~245° C. for about two hours to complete the transesterification reaction. 2.0 mg of antimony triacetate was charged. Vacuum was applied gradually over about 15 min to full vacuum (~0.2 mmHg). The temperature was raised to 245~255° C., and held for three hours, with melt viscosity increasing during the polymerization. The reaction was stopped and polymer was obtained.

Polymer was placed in a non-stick pan and placed in a vacuum oven at room temperature. The vacuum oven was reduced to a vacuum below 1 mmHg, and the temperature of the oven was then increased gradually to 200° C. over 3 hrs. The specimen was finally held at 200° C. and 0.5 mmHg for 48 hours. After the oven was cooled to room temperature, the specimen was removed.

The polymers of Examples 6-18 are listed in Table 1 for ease of reference. The results of some simple calculations based on the polymers' structures are shown in Table 2. Glass transition temperatures for the polymers, obtained as described in the Test Methods, are also shown in Table 2.

TABLE 1

The Polymers of Examples 6-18

| Ex. No. | Diacid Monomer (Backbone Atoms) | Diol Monomer (Backbone Atoms) |
|---|---|---|
| 6 | fluorene dipropionic ester (7) | ethylene glycol (4) |
| 7 | fluorene dipropionic acid (7) | butanediol (6) |
| 8 | fluorene dipropionic acid (7) | F9-diethanol (7) |
| 9 | fluorene dipropionic ester (7) | fluorene dipropanol (9) |
| 10 | difluorene ethane dipropionic ester (10) | ethylene glycol (4) |
| 11 | difluorene ethane dipropionic ester (10) | butane diol (6) |
| 12 | difluorene ethane dipropionic ester (10) | fluorene dipropanol (9) |
| 13 | difluorene ethane dipropionic ester (10) | difluorene ethane dipropanol (12) |
| 14 | difluorene methane dipropionate ester (9) | ethylene glycol (4) |
| 15 | difluorene methane dipropionate ester (9) | difluorene methane dipropanol (11) |
| 16 | difluorene methane dipropionate ester (9) | butane diol (6) |
| 17 | fluorene succinic acid backbone (4) | butane diol (6) |
| 18 | fluorine dipropionic acid with tails (7) | fluorine dipropanol (9) |

TABLE 2

Structural Calculations and Glass Transition Temperatures of the Polymers of Examples 6-18.

| Ex. No. | Back Bone Length (atoms) | Phenyl Rings | Rings per Backbone Atom | Tg (C.) |
|---|---|---|---|---|
| 6 | 11 | 2 | 0.18 | 67.0 |
| 7 | 13 | 2 | 0.15 | 53.5 |
| 8 | 14 | 2 | 0.14 | 52.5 |
| 9 | 16 | 4 | 0.25 | 95.7 |
| 10 | 14 | 4 | 0.29 | 116.5 |
| 11 | 16 | 4 | 0.25 | 104.0 |
| 12 | 19 | 6 | 0.32 | 124.5 |
| 13 | 22 | 8 | 0.36 | 145.0 |
| 14 | 13 | 4 | 0.31 | 107.0 |
| 15 | 20 | 8 | 0.40 | 127.1 |
| 16 | 15 | 4 | 0.27 | 90.4 |
| 17 | 10 | 2 | 0.20 | 68.3 |
| 18 | 16 | 4 | 0.25 | 73.0 |

Preparation of Polymer Films

A film was prepared from each of the polymers of Examples 6-18. For each, a specimen was dried for 48 hrs at 70 C in a vacuum oven at a pressure less than 1 mmHg Once dry, the specimen was removed and promptly melt-pressed at 220° C. between polyimide sheets into a plaque of 5 mil thickness. The glass transition temperature of the polymer was determined via DSC as described in the Test Methods. The pressed specimen was cut into stretching specimens which were squares of 1 cm² in size. A stretching specimen was clamped with pliers on opposing edges and heated over a heat gun to 5-15 C above the glass transition temperature. The heated stretching specimen was then drawn by pliers-stretching by hand at a rate of about 100%/sec, to a final stretch ratio of about 6×. Each specimen contracted in the planar direction normal to the stretch direction by about a factor of 2 (nominal transverse stretch ratio of 0.5), resulting in a stretched film specimen having stretch ratios of approximately 6×0.5.

Test Methods

Differential Scanning Calorimetry

Pressed film specimens were tested under nitrogen using DSC (Q2000 commercially available from TA Instruments, New Castle, Del.). A test specimen of about 5-10 mg was used for each test. The test employed a 3 stage heating-cooling-heating temperature ramp protocol. The test specimen was heated from 30 to 300° C., then cooled back down to 30° C., and then heated for a second time to 300° C., all at a rate of 20° C./min. The test specimen was held at 300° C. for 3 min after the first heating. The cooling scan and the second heating scan were analyzed. The cooling scan from 300 to 30° C. was analyzed for crystallization temperature from the melt ($T_c$).

The second heating scan from 30 to 300° C. was analyzed for glass transition temperature ($T_g$), cold crystallization temperature ($T_{cc}$, also known as the crystallization temperature from the glass), and melting temperature ($T_m$).

Measured values for Tg of each of the polymers of Examples 6-18 are shown in Table 2. None of the polymers of Examples 6-18 exhibited a $T_c$, a $T_{cc}$, or a $T_m$, indicating that the Exemplary polymers were all amorphous.

Refractive Index (RI)

The refractive indices of specimens of unstretched pressed films, and stretched films, made from each polymer of Examples 6-18 were measured using a Metricon Prism Coupler (Metricon Corporation, Pennington, N.J.). RI of each stretched film specimen was determined in each of the machine direction (stretch direction), transverse direction (planar direction normal to the stretch direction), and thickness direction (direction normal to the film plane). These directions are designated MD, TD, and TM, respectively. Thus, MD and TD are in-plane directions and TM is normal to the film surface. The refractive indices in MD, TD and TM are labeled as $n_x$, $n_y$, and $n_z$, respectively.

Using the Metricon method for RI, it is only possible to measure two of the three orthogonal refractive indices simultaneously. Typically, the x and z directions are measured in one test, and the y and z are measured in a second test. Sometimes it is difficult to calculate the refractive index in a given direction accurately due to the lack of a sharp "knee" in the Metricon data. Table 3 shows refractive index data obtained for the polymers of Examples 6-18. For some specimens, it was difficult to obtain a clear y-direction refractive index. For some specimens, it was difficult to obtain a clear z-direction index when the z-direction index was measured along with the x-direction index. For some specimens, it was difficult to obtain a clear z-direction index when the z-direction index was measured along with the y-direction index. However, it was possible to obtain at least one value for the z-direction index by combining the data from both sets of measurements. Thus, birefringence was calculated as the difference between the x-direction index, and the only, or higher, value obtained for the z-direction index.

The results are shown in Table 3. It can be seen that all the polymers of Examples 6-18 exhibit negative birefringence upon stretching. However, Example 17, the only polymer for which the fluororene-containing pendant is attached to the chain via a linkage that allows for rotation of the fluorene-containing pendant (i.e., the only polymer in which the pendent fluorine is not conformationally locked), exhibits a negative birefringence that is much smaller in absolute value than those of the other Examples.

TABLE 3

Refractive Index and Birefringence Data for the Polymers of Examples 6-18

| Ex. No. | Bulk RI | RI(x) (Stretch Direction) | RI(y) (Transverse Direction) | RI(z) (Thickness Direction) (as measured with x direction) | RI(z) (Thickness Direction) (as measured with y direction) | Max RI(z) from the two measurements | ΔRI(xz) (using Max RI(z)) |
|---|---|---|---|---|---|---|---|
| 6 | 1.5956 | 1.5798 | 1.5984 | * | 1.6021 | 1.6021 | −0.0223 |
| 7 | 1.5868 | 1.5732 | 1.5914 | 1.5907 | 1.5906 | 1.5907 | −0.0175 |
| 8 | 1.5098 | 1.5003 | 1.5132 | 1.5139 | 1.5136 | 1.5139 | −0.0136 |
| 9 | 1.6112 | 1.5881 | 1.6184 | 1.6229 | 1.6194 | 1.6229 | −0.0348 |
| 10 | 1.6160 | 1.5907 | * | 1.6263 | * | 1.6263 | −0.0356 |
| 11 | 1.6107 | 1.5888 | * | * | 1.6198 | 1.6198 | −0.0310 |
| 12 | 1.6231 | 1.5859 | * | * | 1.6332 | 1.6332 | −0.0473 |

TABLE 3-continued

Refractive Index and Birefringence Data for the Polymers of Examples 6-18

| Ex. No. | Bulk RI | RI(x) (Stretch Direction) | RI(y) (Transverse Direction) | RI(z) (Thickness Direction) (as measured with x direction) | RI(z) (Thickness Direction) (as measured with y direction) | Max RI(z) from the two measurements | ΔRI(xz) (using Max RI(z)) |
|---|---|---|---|---|---|---|---|
| 13 | 1.6244 | 1.5907 | * | * | 1.6441 | 1.6441 | −0.0534 |
| 14 | 1.6227 | 1.5928 | 1.6337 | 1.6398 | 1.6393 | 1.6398 | −0.0470 |
| 15 | 1.6352 | 1.6037 | 1.6422 | 1.6527 | 1.6505 | 1.6527 | −0.0490 |
| 16 | 1.6167 | 1.5911 | 1.6274 | 1.6303 | 1.6303 | 1.6303 | −0.0392 |
| 17 | 1.5953 | 1.5944 | 1.5951 | 1.5948 | 1.5949 | 1.5949 | −0.0005 |
| 18 | 1.6016 | 1.5937 | 1.6133 | 1.6154 | * | 1.6154 | −0.0217 |

* Could not be measured due to lack of a sharp "knee" in the Metricon data.

Examples 19 and 20

Stretched Layered Polymer Films

Extrusion coated and batch-stretched layered films in which one layer comprised Poly ethylene 3-{9-[9-(2-Ethoxy-carbonylethyl)-9H-fluoren-9-ylmethyl]-9H-fluoren-9-yl}-propionate (also known as Poly ethylene difluoryl methyl propionate, or PEDMP), were prepared. PEDMP is the same polymer as that prepared in Example 14, but was prepared as described below.

PETN80 was used for the other layer in each layered film. PETN80 is the designation for a copolyester nominally having 20 mol % terephthalate moieties and 80 mol % 2,6-naphthalate moieties, on an acids basis, and 100 mol % ethylene glycol moieties on a diols basis.

PETN80 resin was prepared as follows. To a room temperature stainless steel 10-gallon reactor kettle equipped with oil-jacketed heating, an overhead separation column, and a vacuum pump, the following were added:

36.28 lbs. of dimethyl 2,6-napthalenedicarboxylate (0.1485 lbmols)

7.21 lbs. of dimethyl terephthalate (0.0371 lbmols)

28.8 lbs. of ethylene glycol (0.464 lbmols)

30.0 g of trimethylolpropane (crosslinker)

7.9 g of antimony triacetate (as a catalyst)

3.0 g of zinc acetate (as a catalyst)

4.9 g of cobalt acetate (as a catalyst)

The reaction mixture was heated and stirred at 125 rpm under 20 psig of $N_2$. The temperature was raised over the course of about 1.5 hours to 250° C. By-product methanol was driven off and collected in the overheads receiver. The pressure in the kettle was then slowly reduced to atmospheric, and 7.9 g of triethyl phosphono acetate was added to the reactor. After 5 more minutes of stirring a vacuum was applied to the kettle. After stirring at about 50 rpm for about 1.5 hours at a temp of about 280° C. under vacuum (pressure of 1-5 mmHg), the reaction mixture reached the target endpoint, as indicated by an agitator power draw known for this reaction kettle to correlate to the rheology of a PET having an IV of 0.60. The resulting polymer was drained from the kettle into trays. These bricks of polymer resin were allowed to cool and were later ground into small, relatively uniform granules.

The PETN80 granules were dried at 90° C. for 48 hrs. The PETN80 was fed at 9.8 lbs/hr to a 1.25" Killion KL-125 single screw extruder (Killion, Pawcatuck, Conn.) having a length/diameter ratio (l/d) of 24. The extruder temperature was profiled from feed to exit, beginning at 210° C. and rising to 249° C. The extruder was connected by a ½' OD necktube to a monolayer feedblock at 249° C. which fed a 6" wide CW Brabender die. The die was adjusted to cast a monolayer film of about 10 mil thickness, which was quenched on an 8" diameter chill roll at 20° C. and then wound into a stockroll.

PEDMP for these Examples was prepared at larger scale than in Example 14, as follows.

A 3-neck 1-Liter round bottom flask equipped with $N_2$ inlet, distillation apparatus, and mechanical stir bar was charged with 490.25 g 3-{9-[9-(2-Ethoxycarbonylethyl)-9H-fluoren-9-ylmethyl]-9H-fluoren-9-yl}-propionic acid ethyl ester, 134.08 g of ethylene glycol, and 0.25 g of titanium tetrabutoxide. The mixture was heated to 220° C. gradually producing ethanol distillate. The reaction was kept at 220~250° C. for about two and a half hours to complete the transesterification reaction. Vacuum was applied gradually over about 15 min to full vacuum (~0.4 mmHg). The temperature was raised to 250~255° C., and held for three hours, with melt viscosity increasing during the polymerization. The reaction was stopped and polymer was obtained.

The PEDMP was placed in a non-stick pan and placed in a vacuum oven at room temperature. The vacuum oven was pumped down to a vacuum below 1 mmHg, and the temperature of the oven was then increased gradually to 200° C. over 3 hrs. The PEDMP was then held at 200° C. and 0.5 mmHg for 48 hours. After the oven was cooled to room temperature, the sample was removed and ground into relatively uniform granules.

The PEDMP granules were dried at 90° C. for 48 hrs. The PEDMP was fed at about 9.8 lbs/hr to a 1.25" Killion KL-125 single screw extruder (Killion, Pawcatuck, Conn.) having a length/diameter ratio (l/d) of 24. The 3 temperature-zoned extruder was profiled from feed to exit at 182° C., 188° C. and 200° C. The extruder was connected by a ½ OD" necktube to a monolayer die at 200° C. which fed a 6" CW Brabender die. The die was adjusted to cast a PEDMP monolayer film of 6 mils thickness onto a 10 mil PETN80 liner made as described above. The extrusion coated film was quenched on an 8" diameter chill roll at 45° C. and then wound into a stockroll.

The two layer film was placed between two layers of film made from Total 8650 Polypropylene copolymer (Total Petrochemicals, Houston, Tex.), and stretching specimens were cut from the multilayer construction. One stretching specimen (Example 19) of the film was stretched in a KARO IV laboratory-scale batch film stretcher (Brueckner, Siegsdorf, Germany) at about 5-10° C. above the glass transition temperature of the PEDMP layer, to a stretch ratio of 5×1, with the specimen's sides constrained (to simulate stretching behavior typical of the crossweb stretch in a conventional film tenter). Another stretching specimen of the film (Example 20)

was simultaneously biaxially stretched in the KARO IV at the same temperature to a stretch ratio of 2.9×2.9. For each of the two stretched films, refractive indices of the PEDMP layer, in x, y, z directions, were measured using a Metricon Prism Coupler (Metricon Corp.—Pennington, N.J.). The birefringence between the x and z directions was also calculated. Results are reported in Table 4. The results obtained earlier for the film of Example 14 are also shown for comparison.

TABLE 4

Refractive Indices of PEDMP Layers in Stretched Monolayer and Multilayer Films.

| Example No. | Stretching Mode | Stretch Ratio | RI(x) | RI(y) | RI(z) | ΔRI(xz) |
|---|---|---|---|---|---|---|
| 14 | Uniaxial Unconstrained | 6 × 0.5 | 1.5928 | 1.6337 | 1.6398 | −0.0470 |
| 19 | Uniaxial Constrained | 5 × 1 | 1.5990 | 1.6311 | 1.6361 | −0.0371 |
| 20 | Simultaneous Biaxial | 2.9 × 2.9 | 1.6184 | 1.6177 | 1.6354 | −0.0170 |

What is claimed is:

1. A multilayer optical film comprising:
   at least one first birefringent optical layer; and
   at least one second optical layer having a lower birefringence than the first optical layer; wherein at least one of the optical layers comprises a negatively birefringent polyester polymer comprising a backbone and repeat units comprising at least one pendent aromatic group that is conformationally locked relative to the backbone.

2. The multilayer film of claim 1 wherein parallel sides of the pendent aromatic group are orthogonal to the polyester polymer backbone.

3. The multilayer film of claim 1 wherein the aromatic group is a fluorene group.

4. The multilayer film of claim 1 wherein the second optical layer comprises the polyester polymer repeat units comprising at least one pendent fluorene group.

5. The multilayer film of claim 1 wherein the backbone is free of aromatic groups.

6. The multilayer film of claim 1 wherein the polyester polymer is derived from at least one diacid, diester, diol, or mixture thereof comprising at least one pendent fluorene group.

7. The multilayer film of claim 1 wherein the polyester polymer is derived from at least difluorene diol.

8. The multilayer film of claim 1 wherein the polyester polymer is derived from a difluorene monomer selected from the group consisting of difluorene diols, difluorene methylene diesters, and difluorene methylene diacids.

9. The multilayer film of claim 1 wherein the polyester polymer is derived from non-aromatic diols.

10. The multilayer optical film of claim 1 wherein the polyester polymer has a glass transition temperature ranging from 50° C. to 200° C.

11. The multilayer optical film of claim 1 wherein the second optical layer has a negative in-plane birefringence at 632.8 nm after the multilayer film is formed.

12. The multilayer optical film of claim 11 wherein the second optical layer has an in-plane birefringence at 632.8 nm ranging from −0.01 to −0.06 after the multilayer film is formed.

13. The multilayer optical film of claim 1 wherein the multilayer optical film is a polarizer or a mirror.

14. The multilayer optical film of claim 1 wherein the multilayer comprises a plurality of first optical layers alternating with a plurality of second optical layers.

15. A multilayer optical film comprising:
   at least one first birefringent optical layer; and
   at least one second optical layer having a lower birefringence than the first optical layer; wherein at least one of the optical layers comprises a polyester polymer comprising repeat units comprising at least one pendent fluorene group.

16. The multilayer film of claim 15 wherein the pendent fluorene group is bonded directly to the polyester polymer backbone.

17. The multilayer film of claim 15 wherein the repeat units comprise a monofluorene, a difluorene, or a combination thereof.

18. The multilayer film of claim 15 wherein 20 to 100 mol-% of the repeat units comprise the pendent fluorene groups.

19. An oriented polyester film comprising a negatively birefringent polyester polymer comprising a backbone and repeat units comprising at least one pendent aromatic group that is conformationally locked relative to the backbone.

20. A negatively birefringent polyester polymer comprising a backbone and repeat units comprising at least one pendent aromatic group that is conformationally locked relative to the backbone.

21. A difluorene monomer selected from the group consisting of difluorene diols, difluorene methylene diesters, and difluorene methylene diacids.

22. The difluorene monomers of claim 21 wherein the difluorene monomer has the general formula:

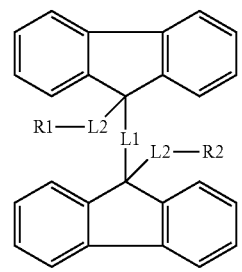

wherein R2 is OH and L1 and L2 are independently a bond or non-aromatic linking groups.

23. The difluorene monomers of claim 21 wherein the difluorene monomer has the general formula:

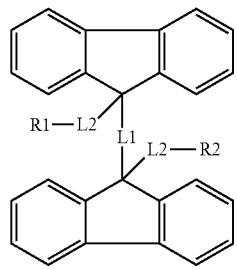

wherein L1 is methylene, L2 are independently a bond or a non-aromatic linking group, and R1 and R2 are independently hydroxyl or a group comprising a carbonyl.

24. The fluorene monomer of claim 23 wherein L2 are independently alkylene groups.

25. The fluorene monomer claim 21 wherein at least one of the aromatic rings of at least one fluorene further comprises a substituent.

26. A polyester polymer prepared from a fluorene monomer of claim 21.

* * * * *

UNITED STATES PATENT AND TRADEMARK OFFICE
CERTIFICATE OF CORRECTION

| | | |
|---|---|---|
| PATENT NO. | : 8,854,730 B2 | |
| APPLICATION NO. | : 13/303881 | |
| DATED | : October 7, 2014 | |
| INVENTOR(S) | : Lei Wang et al. | |

It is certified that error appears in the above-identified patent and that said Letters Patent is hereby corrected as shown below:

Title Page

Page 2, Column 2 (Other Publications)
Line 26, delete "Alchols" and insert -- Alcohols --, therefor.

In the Specification

Column 5
Line 51, delete "(e.g. fluoroene)" and insert -- (e.g. fluorene) --, therefor.

Column 6
Line 33, delete "fluoroene" and insert -- fluorene --, therefor.

Column 7
Line 61, delete "aralkyaryl" and insert -- alkaryl --, therefor.

Column 8
Line 67, delete "dipropanionate" and insert -- dipropionate --, therefor.

Column 9
Line 7, after "fluorene or" delete "other".

Line 20, delete "(e,g, homopolymer)" and insert -- (e.g. homopolymer) --, therefor.

Column 10
Line 48, after "fluorene or" delete "other".

Signed and Sealed this
Second Day of June, 2015

Michelle K. Lee
*Director of the United States Patent and Trademark Office*

Column 11
Line 44, before "up to" delete "up".

Line 67, delete "posively" and insert -- positively --, therefor.

Column 12
Lines 36-37, delete "birefriengence" and insert -- birefringence --, therefor.

Column 14
Line 36, delete ""Chimmasorb" and insert -- "Chimassorb --, therefor.

Column 16
Line 48 (approx.), delete "Aluminun" and insert -- Aluminum --, therefor.

Line 56 (approx.), delete "napthalenedicarboxylate" and insert -- naphthalenedicarboxylate --, therefor.

Column 25
Line 20 (approx.), delete "30 C." and insert -- 30° C. --, therefor.

Line 21 (approx.), delete "0.485 dL/g" and insert -- 0.485 dL/g. --, therefor.

Column 30
Line 45, delete "flurorene-" and insert -- fluorene- --, therefor.

Line 45, delete "catalyst)" and insert -- catalyst). --, therefor.